United States Patent [19]

Hardman

[11] Patent Number: 4,939,666
[45] Date of Patent: Jul. 3, 1990

[54] INCREMENTAL MACROMOLECULE CONSTRUCTION METHODS

[75] Inventor: Karl D. Hardman, Gaithersburg, Md.

[73] Assignee: Genex Corporation, Gaithersburg, Md.

[21] Appl. No.: 92,147

[22] Filed: Sep. 2, 1987

[51] Int. Cl.$^5$ .................................................. G06F 3/14
[52] U.S. Cl. ...................................... 364/496; 436/86; 436/89; 935/87
[58] Field of Search .............................. 364/496–499, 364/521; 435/172.1, 172.2, 172.3; 436/86, 89; 935/85–88

[56] References Cited

U.S. PATENT DOCUMENTS

| | | | |
|---|---|---|---|
| 4,085,443 | 4/1978 | DuBois et al. | 340/711 |
| 4,205,391 | 5/1980 | Ulyanov et al. | 364/496 |
| 4,266,253 | 5/1981 | Matherat | 364/300 |
| 4,365,303 | 12/1982 | Hannah et al. | 364/498 |
| 4,414,629 | 11/1983 | Waite | 358/257 |
| 4,704,692 | 11/1987 | Ladner | 364/496 |
| 4,719,582 | 1/1988 | Ishida et al. | 364/497 |
| 4,747,059 | 5/1988 | Hirayama et al. | 364/496 |

FOREIGN PATENT DOCUMENTS

| | | |
|---|---|---|
| 130756 | 1/1985 | European Pat. Off. . |
| 155832 | 9/1985 | European Pat. Off. . |

OTHER PUBLICATIONS

Small Business Innovation Phase I Grant Application of Creative BioMolecules, Inc., Aug. 1984.
Small Business Innovation Phase II Grant Application of Creative BioMolecules, Inc., Dec. 1985.
"Computer Aided Model Building Strategies for Protein Design", Pabo et al., *Biochemistry*, vol. 25, p. 5987, (1986).
"Unpaired Cysteine–54 Interferes with the Ability of an Engineered Disulfide to Stabilize T4 Lysozyme", Perry et al., *Biochemistry*, vol. 25, p. 733, (1986).
"Crystal and Molecular Structure of the Inhibitor Eglin from Leeches in Complex with Subtitisin Carlsberg", McPhalen et al., *FEBS Letters*, vol. 188, p. 55, (Aug., 1985).
"A Genetic Screen for Mutations that Increase the Thermal Stability of Phage T4 Lysozyme", Alber et al., *Biochemistry*, vol. 82, p. 747, (Feb., 1985).
"Genes for Alkaline Protease and Neutral Protease from Bacillus amyloliquefaciens Contain a Large Open Reading Frame Between the Regions Coating for Signal Sequence and Mature Protein", *Journal of Bacteriology*, vol. 159, p. 811, (1984).
"Disulfide Bond Engineered Into T4 Lysosome: Stabilization of the Protein Toward Thermal Inactivation", Perry et al., *Science*, vol. 226, pp. 555, (Nov. 2, 1984).
"Using Known Substructures in Protein Model Building and Crystallography", Jones et al., *EMBO J.*, vol. 5, p. 819, (1986).
"Chimeric Human Antibody Molecules: Mouse Antigen–Binding Domains with Human Constant Region Domains", Morrison et al., *Proc. Nat'l Academy of Science U.S.A.*, vol. 84, p. 6851, (1984).
"Production of Functional Chimaeric Mouse/Human Antibody", Boulianne et al., *Nature*, vol. 312, p. 643, (1984).

(List continued on next page.)

*Primary Examiner*—Parshotam S. Lall
*Assistant Examiner*—Brian M. Mattson
*Attorney, Agent, or Firm*—Saidman, Sterne, Kessler & Goldstein

[57] ABSTRACT

A preferred embodiment of the invention is a method for constructing a polypeptide chain having a substantially predetermined conformation. Preferably a known stable well-mapped polypeptide structure is used as a starting point, and additional peptide units are incrementally added on while maintaining favorable enthalpic and entropic contributions to stability. Preferably a library of oligopeptide blocks is used to provide candidates for the additional peptide units. Preferably the library includes numerous precomputed parameters for each of the blocks, e.g. parameters for estimating energetic effects of varying the conformation parameters.

31 Claims, 5 Drawing Sheets

OTHER PUBLICATIONS

"Prediction of the Folding of Short Polypeptide Segments by Uniform Conformational Sampling", Bruccoleri et al., *Biopolymers*, vol. 26, p. 137, (1987).

"The Analysis of Homologous Tertiary Structures and the Design of Novel Proteins", *Protein Engineering Applications*, Barlow et al., p. 29, (ed. Inouye & Sarma, 1986).

"Structure Implications for Macromolecular Recognition and Redesign", Getzoff et al., *Protein Engineering Applications*, p. 41, (ed. Inouye & Sarma, 1986).

"Knowledge-Based Prediction of Protein Structures and the Design of Novel Molecules", Blundell et al., *Nature*, vol. 326, p. 347, (1987).

"Calculating Three-Dimensional Changes in Protein Structure Due to Amino-Acid Substitutions", Snow et al., *Proteins*, vol. 1, p. 267, (1986).

"An Algorithm for Determining the Conformation of Polypeptide Segments in Proteins by Systematic Search", Moult et al., *Proteins*, vol. 1, p. 146, (1986).

INCREMENTAL MACROMOLECULE CONSTRUCTION METHODS

CROSS-REFERENCE TO OTHER APPLICATIONS

The following U.S. Patent Applications of common assignee contain disclosure and claims related to technological areas which the present invention may also be related to. The following applications are identified on this grounds only, to ensure full compliance with the duty of disclosure as presently interpreted by the U.S. Patent Office, and for the convenience of the Examining Corps. In particular, these applications are not admitted to be prior art. They are also not admitted to be related applications. Moreover, Applicant does not represent that the following list is complete:

U.S. Pat. No. 4,704,692, filed Sep. 2, 1986;
U.S. patent application Ser. No. 902,971, filed Sep. 2, 1986, abandoned; and
U.S. Pat. No. 4,853,871, filed Apr. 6, 1986.

BACKGROUND OF THE INVENTION

1. Field of the Invention

The present application relates to computer assisted methods for making proteins (and other biological materials with similar molecular structure) or other macromolecules artificially, to permit rapid manufacture of macromolecular substances with structures not necessarily found in nature.

2. Discussion of Related Art

Various known teachings, and novel teachings first disclosed in the U.S. Pat. No. 4,704,692, which are believed to be related to various ones of the innovations disclosed in the present application will now be discussed. However, applicant specifically notes that not every idea discussed in this section is necessarily prior art. For example, the characterizations of the particular patents and publications discussed may relate them to inventive concepts in a way which is itself based on knowledge of some of the inventive concepts. Moreover, the following discussion attempts to fairly present various suggested technical alternatives (to the best of applicant's knowledge), even though the teachings of some of those technical alternatives may not be "prior art" under the patent laws of the United States or of other countries. Similarly, the Summary of the Invention section of the present application may contain some discussion of prior art teachings, interspersed with discussion of generally applicable innovative teachings and/or specific discussion of the best mode as presently contemplated, and applicant specifically notes that statements made in the Summary section do not necessarily delimit the various inventions claimed in the present application or in related applications.

Proteins (or polypeptides) are linear polymers of amino acids. Since the polymerization reaction which produces a protein results in the loss of one molecule of water from each amino acid, proteins are often said to be composed of amino acid "residues." Natural protein molecules may contain as many as 20 different types of amino acid residues, each of which contains a distinctive side chain. The particular sequence of amino acid residues in a protein defines the primary sequence of the protein.

Proteins fold into a three-dimensional structure. The folding is determined by the sequence of amino acids and by the protein's environment. The remarkable properties of proteins depend directly from the protein's three-dimensional conformation. Thus, this conformation determines the activity or stability of enzymes, the capacity and specificity of binding proteins, and the structural attributes of receptor molecules. Because the three-dimensional structure of a protein molecule is so significant, it has long been recognized that a means for stabilizing a protein's three-dimensional structure would be highly desirable.

The three-dimensional structure of a protein may be determined in a number of ways. Perhaps the best known way of determining protein structure involves the use of the technique of x-ray crystallography. An excellent general review of this technique can be found in *Physical Bio-chemistry*, Van Holde, K. E. (Prentice-Hall, NJ (1971)) (especially pages 221-239), which is herein incorporated by reference. Using this technique, it is possible to elucidate three-dimensional structure with remarkable precision. It is also possible to probe the three-dimensional structure of a protein using circular dichroism, light scattering, or by measuring the absorption and emission of radiant energy (Van Holde, *Physical Biochemistry*, Prentice-Hall, NJ (1971)). Additionally, protein structure may be determined through the use of the techniques of neutron diffraction, or by nuclear magnetic resonance (*Physical Chemistry*, 4th Ed. Moore, W. J., Prentice-Hall, NJ (1972) which is hereby incorporated by reference).

The examination of the three-dimensional structure of numerous natural proteins has revealed a number of recurring patterns. Alpha helices, parallel beta sheets, and anti-parallel beta sheets are the most common patterns observed. An excellent description of such protein patterns is provided by R. Dickerson et al., *The Structure and Action of Proteins* (1969). The assignment of each amino acid to one of these patterns defines the secondary structure of the protein. The helices, sheets and turns of a protein's secondary structure pack together to produce the three-dimensional structure of the protein. The three-dimensional structure of many proteins may be characterized as having internal surfaces (directed away from the aqueous environment in which the protein is normally found) and external surfaces (which are in close proximity to the aqueous environment). Through the study of many natural proteins, researchers have discovered that hydrophobic residues (such as tryptophan, phenylalanine, tyrosine, leucine, isoleucine, valine, or methionine) are most frequently found on the internal surface of protein molecules. In contrast, hydrophilic residues (such as aspartate, asparagine, glutamate, glutamine, lysine, arginine, histidine, serine, threonine, glycine, and proline) are most frequently found on the external protein surface. The amino acids alanine, glycine, serine and threonine are encountered with equal frequency on both the internal and external protein surfaces.

Proteins exist in a dynamic equilibrium between a folded, ordered state and an unfolded, disordered state. This equilibrium in part reflects the interactions between the side chains of amino acid residues which tend to stabilize the protein's structure, and, on the other hand, those thermodynamic forces which tend to promote the randomization of the molecule.

The amino acid side chain interactions which promote protein folding and confer catalytic activity fall into two classes. The interactions may be caused by weak forces (e.g. hydrogen bonds) between the side chains of different amino acid residues. Alternatively, they may be caused by direct covalent bonding between the sulfhydryl groups of two cysteine amino acid residues. Such a bond is known as a "disulfide" bond.

When a protein is synthesized, any cysteine residues present contain free sulfhydryl groups (—SH). When two sulfhydryl groups in close proximity are mildly oxidized, disulfide bonds (—S—S—) may form, thereby crosslinking the polypeptide chain. The formation of this chemical bond is said to convert two "cysteine" residues into a "cystine" residue. Thus "cysteine" residues differ from a "cystine" residue in that the former molecules contain sulfur atoms which are covalently bonded to hydrogen, whereas the latter molecule contains a sulfur atom which is covalently bonded to a second sulfur atom.

A disulfide bond may stabilize the folded state of the protein relative to its unfolded state. The disulfide bond accomplishes such a stabilization by holding together the two cysteine residues in close proximity. Without the disulfide bond, these residues would be in close proximity in the unfolded state only a small fraction of the time. This restriction of the conformational entropy (disorder) of the unfolded state destabilizes the unfolded state and thus shifts the equilibrium to favor the folded state. The effect of the disulfide bond on the folded state is more difficult to predict. It could increase, decrease or have no effect on the free energy of the folded state. Increasing the free energy of the folded state may lead to a destabilization of the protein, which would tend to cause unfolding. Importantly, the cysteine residues which participate in a disulfide bond need not be located near to one another in a protein's primary amino acid sequence.

One potential way of increasing the stability of a protein is to introduce new disulfide bonds into that protein. Thus, one potential application of recombinant DNA technology to the stabilization of proteins involves the introduction of cysteine residues to produce intraprotein disulfide bonds. There are two ways in which cysteine residues may be introduced into a protein: (1) through a replacement-exchange with one of the protein's normally occurring amino acid residues, or (2) an insertion of a cysteine between two existing amino acid residues.

Recently, investigators have employed computers and computer graphics displays as an aid for assessing the appropriateness of potential linkage sites. See Perry, L. J., & Wetzel, R., *Science*, 226:555–557 (1984); Pabo, C. O., et al., *Biochemistry*, 25:5987–5991 (1986); Bott, R., et al., European Patent Application Serial Number 130, 756; Perry, L. J., & Wetzel, R., *Biochemistry*, 25:733–739 (1986); and Wetzel, R. B., European Patent Application Serial Number 155,832; all of which are hereby incorporated by reference. The methods developed by Wetzel and co-workers permit one to project the three-dimensional conformation of a protein onto a computer screen and to simulate the effect which a disulfide bond might have on the protein's structure. Although these methods facilitate the design of more stable proteins, the researcher must still select the amino acid residues which are to be replaced by the cysteine residues of the disulfide bond. Hence, a substantial amount of guess work and trial and error analysis are still required. A need, therefore, still exists where a method which will assist the user in selecting potential disulfide bond linkage sites.

POLYPEPTIDE SEQUENCE 3-D STRUCTURE

As extensively discussed in the U.S. Pat. No. 4,704,692, the field of protein engineering is an area of very high and increasing activity. The potential ability to manufacture customized antibodies (or hormones, enzymes, receptors, inhibitors, repressors, etc.) would be of tremendous diagnostic, therapeutic, and research utility. The new capability in this area promises to permit a technological revolution of immense impact.

Genetic engineering now permits essentially arbitrary polypeptide chains to be manufactured routinely. In principle, any desired sequence of the standard peptide units can be manufactured as a polypeptide chain by generating a DNA sequence and expressing it (for example, in *E. coli* or *B. subtilis*, *S. cerevisiae* or other yeast, or mammalian cells). For example, the state of the art in 1987 is such that any desired single chain polypeptide of moderate length (e.g. up to 200 peptide units) can generally be manufactured within 6 months of receiving a polypeptide sequence specification. Longer chains can also be routinely fabricated, though the required delay may be longer. The cost, delay, reliability, and available complexity are all improving very rapidly.

Note that the previous paragraph referred to any desired polypeptide unit rather than to any desired protein. That is, while essentially any given sequence of polypeptides can be routinely manufactured as a linear polypeptide chain, there is no commonly available method for designing a polypeptide sequence that will assume a desired three-dimensional conformation. As is well known, the three-dimensional structure of proteins is critical to their operation. See, for instance, G. Schulz and R. Schirmer, *Principles of Protein Structure* (1979), which is hereby incorporated by reference.

Thus, the available manufacturing techniques have greatly surpassed the design techniques. The number of polypeptide sequences is so large (with 20 common side chain residues possible at each peptide unit) that random variation is not an economical way to obtain an active protein with a desired three-dimensional structure. The full benefit of the available genetic engineering techniques will not be realized until it is possible to predict with confidence what three dimensional structure will result from an artificially designed peptide sequence.

ANTIBODIES

One particular area where the impact of this revolution is likely to arrive soon is in the area of antibodies. Antibodies are binding proteins which have very specific affinities, and can be utilized for many purposes. For example, customized antibodies can be used to detect the presence of any desired agent in the body. (That is, an antibody which has complementarity-determining regions tailored to a specific macromolecule can be used to detect the presence of that macromolecule with extremely high selectivity, and in principle it should be possible to design an antibody which has specificity for almost any given macromolecule. More precisely, since antibodies match to the surface conformation of their complements, any two macromolecules with different surface conformations (or with significantly different characteristics) within any sufficiently small area of their surfaces should in principle be distinguishable by appropriately targeted antibodies. Therefore, these three-dimensional properties can be used to identify and separate (distinguish between) very similar molecules. For example, they can be used to distinguish cancerous cells from normal cells. They can therefore be used for therapeutic or diagnostic measures with extreme specificity. For example, if an antibody which is specific for a desired antigen (e.g. a particular type of cancer cell) can be generated, that antibody macromolecule can be combined with a toxin or a short-lived radioactive species to selectively attack the target antigen, without attacking normal cells.

Antibodies, like other complex protein structures, are normally composed of one or more compact protein domains. In a typical antibody structure there will be 12 such domains.

An antibody normally includes two active regions (known as "v" regions) which can bind selectively to the corresponding antigen. Each Fv region contains an active site defined by a "variable-light" portion $V_L$, which is formed by a portion of one polypeptide chain, and also by a "variable-heavy" portion $V_H$, which is formed by a portion of another polypeptide chain.

Each domain primarily consists of a single polypeptide chain folded up to make a compact three-dimensional structure. Each of the $V_L$ and $V_H$ domains also includes three loops extending out therefrom. These loops are known as "complementarity-determining regions" (CDRs), because their amino acid sequence and three-dimensional conformation determines what antigen structures the antibody will selectively bind to. (Alternatively, these loops are sometimes referred to as "hypervariable regions.") Typically the body of the domain will contain around 115 residues (i.e. about 115 amino acid residues combined in a polypeptide chain), and the CDR loops will contain about 5-15 residues each.

Each of the Fv regions is connected to two more domains (the $C_L$ and $C_{H1}$ domains) which are connected to the $V_L$ and $V_H$ domains of that Fv region. (This set of four domains (the $C_L$, $C_{H1}$, $V_L$ and $V_H$ domains) is collectively referred to as an "Fab" fragment. Thus, the antibody structure includes two such fragments.) In addition, the antibody also includes four domains which are collectively referred to as the "Fc" fragment. The Fc fragment includes two more pairs of domains (known as $C_{H2}$ and $C_{H3}$ domains). Thus, in the natural structure, each $V_L$ domain is chained together with a $C_L$ domain, and each $V_H$ domain is chained together with three $C_H$ domains.

FOLDING POLYPEPTIDE CHAINS

The domains which provide the large-scale building blocks of a protein's structure are generated by appropriate folding of the polypeptide chains in nature. Prediction of how a given polypeptide chain will fold is not easy, since any one polypeptide chain may have more than one possible folding pathway. Moreover, translation back from a desired three-dimensional structure to a polypeptide sequence which would fold to produce that structure is at least as difficult.

NATURAL SEQUENCES AS STARTING POINTS

One technique normally used to simplify this problem is to use a known natural protein structure as the starting point. This is particularly attractive in the case of antibodies, since the structural framework from which the CDR loops extend tends to be relatively constant from one antibody to another. Thus, in custom-tailoring tailoring antibodies, some workers have proposed starting with a structural framework copied from known antibody structures, and modifying only the CDR regions to obtain a desired specificity. However, this approach may not be useful with other types of protein: antibodies are distinctive in having "hypervariable" (CDR) portions which are so readily distinguishable from the rest of the protein structure.

The limited modifications possible to the CDR portions of antibodies are useful, but the more general problem of protein modification is much more difficult. Since the determinants of protein folding are not well understood, it is a delicate matter to modify a protein structure (to any significant degree) without significant risk that the modified protein will not fold correctly, i.e., that the modified polypeptide sequence will not produce the desired three-dimensional structure.

Jones and Thirup, "Using known substructures in protein model building and crystallography," 5 EMBO J. 819 (1986) (which is hereby incorporated by reference) describes an attempt to use known fragments of useful conformation in designing a structure which will have a desired conformation.

Morrison et al., "Chimeric human antibody molecules: Mouse antigen-binding domains with human constant region domains," 81 Proc. Nat'l Acad. Sci. USA 6851 (1984) (which is hereby incorporated by reference) describes an earlier experiment in antibody modification. Some similar work is reported in Boulianne et al., "Production of functional chimaeric mouse/human antibody," 312 *Nature* 643 (1984) (which is hereby incorporated by reference).

ATTEMPTS TO PREDICT FOLDING

There has been significant attention paid to the problems discussed above.

Bruccoleri and Karplus, "Prediction of the Folding of Short Polypeptide Segments by Uniform Conformational Sampling," 26 *Biopolymers* 137 (1987) (which is hereby incorporated by reference) describes an approach to the problem of homology modeling, i.e. the problem of, given members of a family of homologous proteins that have similar three-dimensional structures, predicting the structure of a new member from its sequence. This article particularly discusses the problem of adequately sampling the conformational space of a polypeptide. One of the suggestions in this article appears to be the use of tests at many intermediate points to limit the number of hypotheses which must be examined. This article uses an available program (CHARMM) for assessing energetic contributions. This article also includes some specific discussion of customtailoring of antibodies.

Barlow et al., "The Analysis of Homologous Tertiary Structures and the Design of Novel Proteins," at p. 29 of *Protein Engineering Applications* (ed. Inouye & Sarma 1986) (which is hereby incorporated by reference) suggests the use of a database of known polypeptide structures as a starting point for polypeptide design.

Getzoff et al., "Structural Implications for Macromolecular Recognition and Redesign," at p. 41 of Protein Engineering Applications (ed. Inouye & Sarma 1986) (which is hereby incorporated by reference) provides a very good review of polypeptide structural determinants, and many suggestions as to how these determinants can be taken into account in predicting conformation from sequence, and in modifying polypeptide structures.

Blundell et al., "Knowledge-based prediction of protein structures and the design of novel molecules," 326

Nature 347 (1987) (which is hereby incorporated by reference) also provides suggestions as to how structural determinants can be taken into account in predicting conformation from sequence, and in modifying polypeptide structures.

The article by Snow and Amzel entitled, "Calculating Three-Dimensional Changes in Protein Structure Due to Amino-Acid Substitutions," 1 *Proteins* 267 (1986) (which is hereby incorporated by reference) provides good background on the tweaking steps which can optionally be used as a further level of optimization, e.g. for optimization after having initially added a block or constructed a chain.

Moult and James, "An algorithm for Determining the Conformation of Polypeptide Segments in Proteins by Systematic Search," 1 *Proteins* 146 (dated 1986, but believed to have been actually published in about April 1987) (which is hereby incorporated by reference) describes, as the title suggests, a method for finding known sequence conformations.

European Patent Publication number 0155832 describes modification of known protein structures to introduce disulfide bonds to increase stability. This patent application lists Ronald Wetzel as inventor.

Perry & Wetzel, "Disulfide Bond Engineering into T4 Lysozyme: Stabilization of the Protein Toward Thermal Inactivation," 226 Science 555 (1984), also describes modification of known protein structures to introduce disulfide bonds to increase stability.

SINGLE-CHAIN ANTIBODIES

The U.S. Pat. No. 4,704,692 taught a method for making more significant modifications to protein structure. Included among the extensive teachings of that application is a method for constructing one Fv portion of an antibody as a single polypeptide chain. This teaching permitted binding proteins to be designed for rapid manufacture at low cost. Among the teachings of U.S. Pat. No. 4,704,692 was that modification of the two-chain ($V_L$ plus $V_H$) structure could be performed by selecting an appropriate "linker" polypeptide sequence (e.g. by using an expert rule base to make an optimal selection from a data base of experimentally determined polypeptide sequences). The selected linker's known conformation would permit it to be connected between terminal groups in the two separate polypeptide chains which would normally be parts of the Fv region. A new polypeptide structure could then be defined, with a sequence based on the combination of the known sequence of the $V_L$ and $V_H$ groups and of the linker. This new structure could then be manufactured with substantially reduced risk that the polypeptide chain thus specified would fail to fold successfully into the protein structure desired.

RANGE OF ANALOGOUS STRUCTURES

It is recognized by those skilled in the art that many of the considerations which apply to synthesis of customized antibodies also apply to synthesis of more complex proteins and to analogous complex molecules of other types. It is also recognized that many such complex structures would be extremely useful if they could be built. However, the same problem of primitive design tools has precluded the utilization of the available fabrication techniques.

For example, more complex protein structures often contain a metal ion combined with a structure which is predominantly a polypeptide structure (in such molecules, a porphyrin structure may also be incorporated to link the metal ion to the polypeptide structure). Familiar examples of this type include hemoglobin and cytochrome. Structures of this general kind (i.e. which include metal ions and a large polypeptide sequence) occur in a vast number of enzymes, and are important in many biologically significant processes, as is well known to those skilled in the art.

For another example, glycoproteins (which contain a folded polypeptide portion combined with a carbohydrate structure) are biologically extremely important classes of compounds (for example, they are common constituents of virus coats). Lipoproteins (which contain one or more polypeptide sequences combined with lipid molecules) are also biologically extremely important. It would be desirable to be able to emulate these classes of compounds.

Moreover, it is also possible to modify the functionality of "protein" structures by including other organic or inorganic additions, as is well known. See, for example, Lehninger, *Principles of Biochemistry* (1982), which is hereby incorporated by reference.

Moreover, many more complex structures are formed by multiple chains of polypeptides which are combined together by disulfide bonds (or otherwise). In some cases, the large-scale structure of the protein includes multiple domains, each of which is predominantly composed of a single polypeptide chain (or part of a single chain) folded together The domains may be formed by different sequentially adjacent portions of a single polypeptide chain, or separate polypeptide sequences may be connected by disulfide bonds (or by various non-covalent bonds, e.g. hydrogen bonds or hydrophobic interactions). The problems of predicting three-dimensional structure from a polypeptide sequence (or from plural polypeptide sequences) still remain, and can be especially difficult in large structures which may contain many polypeptide chains.

Moreover, even more complex structures are formed by assembly of multiple polypeptide domains (or analogous domains) which assemble together. (Virus coats, for example, may be of this type.) The ability to synthesize components to fit into structures of this type would also be highly desirable. Similarly, protein/nucleic acid complexes are also of immense potential importance, and the ability to customize polypeptide structures would provide the potential to design inputs into such complexes.

Thus, it should be understood that, in the present application, references to "protein" structures or to "polypeptide" structures will generally be applicable to analogous structures, such as lipoproteins, glycoproteins, proteins which have other organic or inorganic groups attached, and multi-chain and multi-domain polypeptide structures (e.g. large enzymes and viruses). In all of these cases, analogous issues regarding the relation of polypeptide sequence to prediction of three-dimensional structure persist.

The present invention provides an important innovation in manufacturing a desired three-dimensional structure artificially (as will now be discussed). While the present invention is most immediately and especially applicable to antibodies, the present invention also is expected to have analogous applications in analogous polypeptide structures, and in macromolecules of other types.

SUMMARY OF THE INVENTION

In this section various ones of the innovative teachings presented in the present application will be discussed, and some of their respective advantages described. Of course, not all of the discussions in this section define necessary features of the invention (or inventions), for at least the following reasons: (1) various parts of the following discussion will relate to some (but not all) classes of novel embodiments disclosed; (2) various parts of the following discussion will relate to innovative teachings disclosed but not claimed in this specific application as filed; (3) various parts of the following discussion will relate specifically to the "best mode contemplated by the inventor of carrying out his invention" (as expressly required by the patent laws of the United States), and will therefore discuss features which are particularly related to this subclass of embodiments, and are not necessary parts of the claimed invention; and (4) the following discussion is generally quite heuristic, and therefore focusses on particular points without explicitly distinguishing between the features and advantages of particular subclasses of embodiments and those inherent in the invention generally.

The methods newly disclosed represent a further step in the direction of permitting custom-tailoring of proteins, of complexes of proteins with other molecules, and of other macromolecules.

SINGLE-CHAIN RECONFIGURATION

The methods newly disclosed in the present like those taught in the U.S. Pat. No. 4,704,692, allow an existing multi-chain protein structure to be respecified as a single-chain polypeptide sequence which has a high probability of folding to produce the desired three-dimensional structure (conformation). The present invention provides, in one aspect thereof, an improvement of that method, which provides an even higher probability of defining a polypeptide sequence which will fold to produce the desired conformation.

However, the present invention also has a tremendous range of further applications. In general, the present invention provides a general way to customize polypeptide structures. It also provides a general way to modify an existing or partly-designed polypeptide structure to improve its stability or change and/or improve its activity (or other functional property).

OTHER BINDING PROTEINS

A further class of alternative embodiments is to create other binding proteins. For example, "super-specific" antibodies could be constructed by combining more than six CDR loops in a single active site, using (for example) two merged or combined $F_v$ structures (four domains). While six CDR loops (as in the natural combination of $V_L$ and $V_H$ domains) may in principle be sufficient to perform most antigen-recognition tasks, the ability to design with more CDR loops and/or with a physically larger active site area can give antibody designers a better chance of achieving first-pass functionality for the designed structure, without incurring unexpected complementarities to other macromolecules.

INCREMENTAL CONSTRUCTION

One of the innovative teachings in the present application is that, an incremental method is used to design a customized polypeptide sequence. For example, in embodiments such as those of the principal preferred embodiment of the U.S. Pat. No. 4,704,692 where $V_L$ and $V_H$ portions of an antibody are to be reconfigured as a single polypeptide sequence by adding a "linker" sequence), the present invention teaches that the linker is constructed by an incremental method, where peptide units are added one by one, or in groups of a few at a time, while repeatedly culling the candidate set. By contrast, the principal disclosed embodiment of the U.S. Pat. No. 4,704,692 selected a polypeptide connection substantially as a unit, subject to various selection rules. Thus, the embodiments newly disclosed in the present application provide an immensely increased capability. This capability is applicable not only to problems of this type, but also to more radical creation of macromolecular polypeptide structures.

This incremental method not only saves computer time, but also permits additional functionality to be achieved.

STABILITY IMPROVEMENTS

The innovative methods taught herein not only permit existing conformations to be respecified as single-chain structures, but also permit modifications to be specified for other purposes. For example, the innovative methods disclosed permit the stability of a partially predetermined polypeptide structure to be improved. That is, the incremental construction method permits more parameters to be considered for each peptide block in the polypeptide sequence being added. Thus, the added structure can be better optimized for linkage to the existing structure and for minimization of total energy.

While energetic favorability of the desired conformation does not strictly guarantee that the desired conformation will necessarily result from the corresponding polypeptide sequence (since there are so many steps involved in the folding process), it does improve the chances that the polypeptide sequence will in fact fold to produce the desired conformation. More predictably, the more energetically favorable a given conformation is, the greater are the odds that the polypeptide will stay in that conformation when it reaches it.

Thus, the present invention provides improved energetic optimization of modified polypeptide structures. This improved energetic optimization predictably improves stability, and also predictably improves the chances that the polypeptide sequence specified will in fact fold to the desired conformation.

GEOMETRIC FACTORS IN UNFOLDING

The present invention can contribute to stabilization of the folded conformation geometrically. That is, at least some embodiments of the present invention permit an addition to an existing polypeptide conformation to be routed across the surface of the conformation, so that sequentially added units will bind (e.g. by hydrogen bonding) to units of the underlying structure which are not sequentially adjacent. (Alternatively, of course, the added structure could be routed through space if desired.)

Thus, some embodiments of the present invention permit the added peptide sequence to perform a stabilizing function somewhat analogous to that performed by disulfide bonds (which in some protein structures covalently link separate regions of the polypeptide chain(s) together, and thus serve to hold the structure together once it has folded properly). For example, where the initially specified part of the conformation includes (as is common) portions of a beta sheet structure (i.e. places where a polypeptide chain loops back and forth to form several aligned parallel or antiparallel strands), some embodiments of the present invention permit the added peptide residues to sequentially form links to existing residues from different sequences of the beta sheet, i.e. to existing residues which are physically in proximity (in the desired folded conformation) but are not sequentially adjacent. Thus, the present invention enables the construction of structures wherein the folded conformation is not only more energetically favorable overall, but wherein the energy barrier to unfolding is increased (since the bonding of the added units to the existing structure would first have to be broken).

The kinetics of chain folding obeys familiar thermodynamic constraints. At increasing temperature, the increasing importance of the entropy term means that chain unfolding is increasingly likely. Thus, protein chains in general can be unfolded simply by heating them. The greater the enthalpic contribution from folding the chain, the less propensity the chain will have to unfold at low temperatures (i.e. higher temperatures can be withstood before the chain unfolds and the structure therefore loses its functionality). Thus, one advantage enabled by the present invention is that an existing polypeptide conformation can be modified by incrementally adding units to the surface of the conformation in such a way that the gross energetic contribution (from bonding of the new units to the existing conformation, from the additional interface between the new units and the surrounding solution, and allowing for removal of the old units from the surrounding solution interface) is reasonably favorable, or at least not grossly unfavorable. Thus, reasonably favorable folding kinetics can be maintained.

"EXPERT ASSISTANT" EMBODIMENTS

A further aspect of the present invention is that the incremental method preferably used can be used not only for an expert system-directed computer process running alone, but can also be used for a "expert assistant" type of operation. At present, this is the most preferred mode of operation. That is, in an operating mode of this type, the expert system is able to evaluate hypotheses, perform optimization once a candidate has been generally selected, derive parameters for a given candidate, and otherwise greatly accelerate and improve the quality of decision-making, while also taking advantage of the large-scale direction and insight of a human expert.

MINIMIZING COMPUTATIONAL BURDEN

The optimization process preferably used considers a large number of parameters at each step of a process which may include many steps. Parameters which may be considered include hydrogen bonding to the existing structure, energy optimization of the dihedral angles in the polypeptide sequence being added, energy contributions from exposure of hydrophilic groups to the solution, energy contributions from proximity of hydrophobic groups to hydrophobic groups in the existing conformation, van der Waals energetic contributions with respect to the existing structure, and others as will be detailed below. (Of course, some of these considerations can be omitted and/or others added in various embodiments; but those skilled in the art generally recognize that there are many factors which should ideally be taken into account.) Moreover, at each residue, one of 20 standard amino acid residues can in principle be selected, and ultimately (in order for the three-dimensional structure to be known exactly) the two dihedral angle specifications $\phi$ and psi must be specified for each of the residues. Moreover, the orientation of the side group of each peptide block may have several additional degrees of freedom.

Thus, considered a prior is as an optimization problem, the optimization of polypeptide structures is a rather daunting one. The added structure needs to be globally optimized for a result which can nearly be reduced to a single parameter; but this global result is the joint result of individual contributions from the different peptide blocks. Each of the peptide blocks must be examined for at least several target parameters, and each block has at least 3 degrees of freedom (choice of residue plus the two main dihedral angles) and may have significantly more degrees of freedom.

For example, even if the added structure is to contain only ten amino acid residues, the gross number of candidates would be $20^{10}$, and the number of degrees of freedom for each ten-link candidate in this gross solution set would be in the range of 20–40, depending on how many side-chain conformation angles are permitted by the particular residues in each member of the solution set.

Thus, a priority even such a simple example of peptide construction would appear to be a truly vicious optimization problem, which would not be amenable (by many orders of magnitude) to straightforward attack by existing numerical computation architectures.

INCREMENTAL CONSTRUCTION

However, the present invention contains several novel teachings which permit this problem to be efficiently solved. First, incremental construction of the additional peptide sequence is used. This is not as simple as one might think, since the additional units are interrelated. That is, since the problem is inherently a variational problem, it is necessary as the ultimate result to optimize for the added units as a whole. Thus, it may be necessary in incremental construction to add a unit which is not locally optimal, in order to get to an optimal overall conformation.

DYNAMIC PROGRAMMING

A second teaching of the present invention which is used to help achieve this is a "look ahead" optimization method for incremental construction. In the presently preferred embodiment, this is done using a dynamic programming method for hypothesis culling.

INITIALIZATION

A third problem in an incremental construction method, with problems of the type described, is the problem of choosing a starting point. That is, commonly existing structures will include a special termination group on the end of their polypeptide chain, or they may include chain-ending groups which float freely, or the conformation of the chain end may not be in the desired direction. Thus, integration of added structure with an existing structure is not necessarily straightforward, i.e. it is not necessarily good enough to simply start at the termination of existing structure and build on incrementally. One of the innovative teachings in the present application is that this is done by applying the dynamic programming method of "look ahead"

optimization to the meeting of the added groups with the existing termination also, so that the existing termination (and portions of the sequence of the existing termination, i.e. the existing termination less one group, less two groups, less three groups, etc.) are used as starting hypotheses for the added sequence.

USE OF "GOOD ENOUGH" THRESHOLD

Another innovative teaching of the present invention is that the optimization problem can be greatly simplified by introducing a "good enough" decision threshold. That is, the optimization problem is greatly simplified by recognizing that it is not necessary to achieve a fully optimal solution. In the incremental building process, a given level of a figure of merit can be specified as a target or average figure of merit per unit of sequence. The decision-making process can then be truncated by settling on "good enough" candidates, rather than continuing to search until a fully optimal hypothesis is found. A further alternative version of this is that, where the level of fit does not average out to the "good enough" average level locally, a second level of search procedures can be called up to search more broadly until a "good enough" solution is found.

RESTRICTION ON PARAMETERS $CHI_k$

Another innovative teaching of the present invention is that some of the degrees of freedom of the longer side chain groups are preferably ignored. That is, while the longer standard side chains (such as lysine and arginine) have four degrees of freedom in their side chains (that is, they are not fully specified unless four angle parameters $chi_1$, $chi_2$, $chi_3$ and $chi_4$ are specified, in addition to the two main dihedral angles $\phi$ and psi and the peptide backbone torsion angle omega), most of those side chain conformation angle parameters are ignored during the primary selection pass. Some of these additional parameters ($chi_2$ etc.) will be left unspecified in the longer residues, to avoid unfavorable entropic contributions to the kinetics of folding.

MULTI-PASS OPTIMIZATION

A related point is that the optimization is preferably done as a two-pass (or more) optimization. That is, an incremental construction as described is preferably used to form an initial peptide sequence and conformation specification. One or more additional subsequent optimization passes are then preferably used to optimize the goodness of fit of that hypothesis.

EXPERT/NUMERICAL COMBINATION

A related point is that, in some alternative embodiments, in selecting the sequential units of each hypothesis as to the chain, an expert rule system is preferably used to make the selection with respect to various criteria. A numerical calculation method is then preferably used to locally optimize each hypothesis.

In a further embodiment of this, local optimization of particular hypotheses is performed by fixing the position of the last specified block, but allowing the subsequent block (or the subsequent two blocks) to be varied. This permits the conformation of the individual blocks to be optimized fairly efficiently, without permitting this local optimization to overwhelm the progress toward the global optimization desired.

SELECTIVE NESTING OF RECURSION

One feature of the most preferred embodiments which limits computational burden is selective nesting of recursions; that is, the predefined criterion for average figure-of-merit per step can be used to judge when no hypothesis in the set examined is good enough, and therefore an additional backtracking step can be used (or an exclusion rule temporarily suspended, or a secondary set of candidates introduced).

For example, some embodiments of the present invention (which will be described below) permit alteration of residues in the existing structure only as a second stage of selection. That is, if the first stage of selection does not achieve the target threshold for average figure of merit (or, in expert assistant embodiments, whenever the human operator so indicates), additional hypotheses involving replacement of an existing residue can be examined.

STATIC APPROXIMATION

In the methods used in the most preferred embodiments (as is common in the art), the locations of the atoms are largely treated as fixed. This is a convenient approximation, but is not literally correct: the magnitude of typical thermal energies kT at the temperatures of interest is large enough that many vibrational modes of a typical polypeptide structure will be strongly excited. However, the quasi-static assumptions used do provide a useful approximation, which is good enough to allow the advantages of the many other innovative teachings disclosed in the present application to be realized.

Note that, in some alternative embodiments, factors are introduced which compensate for inaccuracies introduced by this model; for example, rules which tend to prevent the presence of lysine except at the surface prevent errors due to misestimation of the negative entropic contribution which could be caused by constraint of the freedom of the long lysine side-group. For another example, some alternative embodiments include rules which permit such entropic contributions to be assessed without the need to exclude any hypotheses (which would risk overweighting the entropic contributions): for example, the entropic dependence map discussed below can be used to ensure that the entropic contributions of methionine are assessed, without preventing placement of methionine groups at inward-facing locations. This is done by (in effect) overlaying a "soft" surface, representing a freedom-of-movement boundary, over the "harder" surface representing van der Waals radii of the atomic positions (as defined using the static approximation), and assessing intrusions on the "soft" surface with a lower penalty function.

OLIGOPEPTIDE LIBRARY

Another of the innovative teachings of the present invention which helps in performing this difficult construction process is the use of a library which contains blocks of usefully small size with multiple precalculated parameters stored for each block. That is, in the presently preferred embodiment, the library includes a complete list of tripeptide sequences. The number of such sequences is 8000.

Alternatively, a different block size, such as dipeptides or tetrapeptides, could be used in the library. This choice depends on several factors, including the tradeoff between run-time computing burden and the number of parameters which must be stored. However, in any case, it is preferred that the size of the blocks in the library include a full set of blocks of the length of tetrapeptides or shorter.

It should be noted that, in addition to a substantially complete set of oligopeptide blocks of at least one size (i.e. a substantially complete set of tripeptides, a substantially complete set of tetrapeptides, and/or substantially complete set of tripeptides), one advantageous alternative class of embodiments also permits the library to include a number of larger blocks. Thus, for instance, longer sequences and parameters (including conformational parameters) could also be included in the library, e.g. by extraction from known structure specifications as they become available. This could be done, e.g. for sizes up through 8- or 10- peptide chains. In particular, substructures of specific functional relevance could be included. For example, one particularly useful element for tailoring antibody structures would be known CDR loop structures and portions thereof.

In embodiments where multiple sizes of blocks are included in the library, one optional (and preferable) sequence of operations is to try the members of the incomplete set of longer blocks out first. Thus, if one of the available longer blocks provides a convenient match, time will be saved by trying it out before the exhaustive search through the shorter blocks.

For another example, it would also be possible to include "branching" blocks, where a covalent bond unites two polypeptide chains near a terminus of one of them. This would permit efficient emulation of branched polypeptide structures. Such structures are common enough in nature that their importance may be large; one common example is insulin.

In another class of alternative embodiments, non-polypeptide blocks can also be included in the library. For example, oligosaccharide and/or oligonucleotide blocks can be included. This permits design of a wider variety of structures, including nucleotide complexes and glycoproteins. Synthesis of such hybrid types is more difficult than that of simple polypeptides (synthesis of glycoproteins normally requires the presence of enzymes which effect glycosylation after the peptide sequence comes off the ribosome), but the need for such structures may outweigh the additional cost of fabricating them.

SCOPE OF PRECOMPUTED PARAMETERS

One of the innovative teachings of the present application is that substantial advantages are achieved, in the context of methods such as those described, by precomputing and storing a substantial number of parameters with the blocks in the library. These parameters can then be used to reduce the runtime computational burden during the incremental construction process. For each block in the library, stored parameters most preferably include the following. However, it should be understood that subsets or supersets of these could be used instead, in accordance with the broad scope of the teachings set forth.

(1) All local-minimum energy conformations for each block.

(2) Parameters for estimating the dependence of energy on the conformation parameters in proximity to each of the local minimum conformations.

(3) Moreover, each of the blocks in the library preferably includes additional parameters which can be used as input to expert rules. For example, a one-bit logical (or few-bit integer) parameter can be prestored to indicate the degree to which a given block is hydrophobic or hydrophilic.

(4) Optionally, a net favorability parameter can also be prestored with each block. That is, some tripeptide sequences can be considered initially to be regarded as more favorable than others.

(5) Localization parameters are preferably also prestored, which make some of the contributions due to interaction between multiple residue groups much easier to calculate. These parameters may include, for example, parameters indicating the propensity of each side chain to ionize and the location of the resulting localized electric charge, parameters indicating localized propensities to form hydrogen bonding, and others as will be discussed below.

OVERLAPPING FITTING OPERATIONS

The most preferred embodiments use a library of oligopeptide residues, but (usually) only one additional amino acid residue at a time is assembled onto the existing structure. That is, candidate oligopeptide blocks are preferably required to overlap the residue sequence defined by previous selection steps. This means that the extensive precomputed parameter set of the library can be used very efficiently, since each new candidate block is subjected to a quite specific starting condition (i.e. the position and orientation of the beginning (at least) of the candidate block is constrained). This means that the local optimization steps preferably used need optimize over a greatly constrained range of possibilities, which in turn means that more detailed tests for optimization can be used.

By contrast, for example, the approach suggested in the Bruccoleri article does not appear to contain any suggestion of such a sliding fit technique.

DYNAMIC UPDATING

The library is preferably updated automatically as additional structure fragments become known (or as conformational evaluation of additional fragments is performed). For example, structures which have been custom-designed according to the innovative methods disclosed (and, preferably, which have successfully demonstrated functionality (and therefore shown that the expected conformation was in fact achieved)) may themselves be loaded into the library, to shorten subsequent work on similar problems. Moreover, as new characterization data becomes available (from crystallographic methods, or from Nuclear Magnetic Resonance (NMR) spectroscopy, or from other sources) this data is preferably loaded in to update and/or expand the library.

Thus, this updating capability provides the capability to "learn."

Similarly, the results of subsequent calculations can be monitored to retrieve improved values for fitting parameters, so that the library can be further updated in this respect too.

TOP-LEVEL ORGANIZATION OF STEPS

Preferably, a set of multi-peptide building blocks is used to construct the polypeptide sequence one residue at a time. For example, when hypotheses for block $L_{(n+1)}$ are to be selected, blocks $L_{(n)}$ and $L_{(n-1)}$ can be used as indices to the library, to select the 20 triplets beginning with a pair of side chains which match the side chains defined for positions $L_{(n-1)}$ and $L_{(n)}$. Thus, use of multiple precomputed parameters for estimating dependences in the library permits rapid adaptation of the next residue in combination with the values of the previous residues and with the XYZ environment of the residue.

XYZ MAP WITH NON-SPATIAL INFORMATION

Thus, in applying the incremental construction method, an XYZ map of the initially determined structure is used as a starting point. This XYZ map includes not only atomic positions with associated van der Waals radii, to give a space filling model, but also includes a number of other localized parameters which greatly accelerate the innovative procedure for finding an optimal fit to this existing structure. Thus, in the presently preferred embodiment, the XYZ map of the existing structure includes not only atomic positions and radii, but also includes localized dipole moment specifications (this is a six-dimensional parameter), as well as parameters indicating entropic and energetic dependence on modification of the position of groups in the predetermined structure.

INITIAL PATH SELECTION

Initially, the human operator preferably specifies a general path for the linkage. For example, in applications of the type discussed in the U.S. Pat. No. 4,704,692, where the $V_L$ and $V_H$ portions of an Fv structure are to be simulated using a polypeptide single chain structure, one of the objectives will commonly be to stabilize the conformation of the $V_L$ and $V_H$ domains, including their relative positions. Thus, the human operator will typically initially specify that the linker being constructed should run for a significant length along the joint between the two existing domain structures. In general, the general choice of initial path is a high enough level decision that the key question here is really what is the objective to be accomplished. That is, the general direction of the path is an objective which is preferably passed to the expert system and not a decision which the expert system is asked to make.

Of course, as the art progresses, and systems embodying the innovative concepts disclosed become more widely available, it is foreseeable that systems incorporating various of the novel concepts disclosed here may also become able to make such higher-level decisions efficiently.

Given a general specification for path, the expert system is preferably allowed to deviate from it slightly. This permits energetic optimization while preserving compatibility with the initially defined objective.

Thus, the incremental building step starts with an XYZ map of various localized factors, together with a general direction and a starting partial sequence. The starting partial sequence is then used to look up additional blocks in the library. The additional blocks in the library will preferably match to the previously determined two residues and, using tripeptide blocks, will enable rapid examination of the 20 candidates for the next residue.

EXAMINATION OF CANDIDATES

The sequence of examination of candidates is preferably as follows. However, this sequence can of course be widely modified and varied. In general, the criteria in selecting a sequence for factor evaluation is that factors which will rapidly dispose the most hypotheses should be examined first. Note that where this sequence of examination gives a non-optimal result (as it sometimes will) a backtracking step is preferably used to permit a wider range of hypotheses to be examined.

In the presently preferred embodiment, the next step performed is a check for gross spatial fit. This can be performed using a variety of algorithms, many of them derived from computer graphics representations.

A salt bridge check is preferably performed next. Since the energy contributions from electrostatic forces can be large, they are preferably assessed early, in order to discard as many unsuitable candidates as possible as soon as possible.

In the presently preferred embodiment, the third step preferably performed is a check for hydrogen bonding.

pH-DEPENDENT CUSTOMIZATION

Another of the innovative teachings of the present invention is that polypeptide structures can be customized for different pH conditions. That is, a group which is to operate in a very alkaline environment can be optimized for a high pH, and a group which is to operate in the human bloodstream can be optimized to a pH of 7.4. That is, one class of preferred embodiments converts the library pK values into localized fractional charge values, once the environmental pH which is relevant to the particular structure is known. This provides a substantial improvement in assessing the contributions due to salt bridges. It also provides substantial advantages in the capability to customize structures for a variety of pH environments.

CLOSURE

Another significant point in choosing the path is that an integer-arithmetic constraint appears here: the constructed polypeptide sequence must have precisely an integral number of peptide units in it. This means that some special attention may be necessary to complete construction of the additional structure without adding an excessive number of amino acid residues.

MIDPOINT CLOSURE

In one alternative class of embodiments, parallelism is facilitated, and the problem of bridging the gap with an integral number of units is also facilitated, by beginning construction from both of the end points and working in parallel towards a gap in the middle. A joint optimization step can then be used to close the gap in the middle.

PARALLEL CONSTRUCTION

In a further class of alternative embodiments, this technique is further extended to permit construction of much more general structures incrementally. For example, where a structure is initially specified which has multiple free ends, completion of the structure can be performed by adding units incrementally onto all of the free ends in parallel. This permits the joint interaction of the units being constructed to be taken into account without presenting an impossible computational burden. In embodiments of this type, a library which includes the standard varieties of reverse turn is preferably used, so that each of the possible closures can be examined as a hypothesis at each step, so that the structure can be rapidly completed. Again, this may be advantageous when it is desired to simulate a complex natural structure by taking only a portion of that natural structure as the starting point and building outwardly therefrom.

SUBSTITUTIONS INTO THE EXISTING STRUCTURE

A full-up optimization process should ideally be able to modify the existing structure slightly, as well as add thereto. An optimization method must take account of the fact that the added structure may hinder the freedom of movement of exposed side groups in the existing structure, and therefore provide negative entropic contributions (e.g. where the existing structure had lysine or arginine tails at its surface.)

In alternative embodiments of the present invention, it is also made possible to substitute residues in the existing structure. For example, where the existing structure has a lysine or arginine residue at its surface, it is likely that added structures will not be able to match well to existing structure in this location. Where the probability density of such long chain residues is high, there may be no path for the incremental structure to be added without passing close to one of the existing lysine or arginine sites. Thus, there is more room to achieve a good solution if it is possible to replace existing groups.

However, there are two constraints on replacing existing groups. First, it must be done with caution, and it should be done using closely akin residues if possible. This minimizes the chances of producing an unfavorable effect which would disrupt the folding process. Secondly, the computational burden could be greatly increased if too much freedom in changing the existing structure is permitted.

One class of embodiments of the present invention therefore permits alteration of residues in the existing structure only as a second stage of selection. That is, if the first stage of selection does not achieve the target threshold for average figure of merit (or, in expert assistant embodiments, whenever the human operator so indicates), additional hypotheses involving replacement of an existing residue can be examined.

At some point, where it is desired not to distort the existing structure, the existing structure is preferably assessed to see if will be distorted by the modifications being considered. Therefore, at some point the existing structure (in such alternative embodiments) will not be treated as rigid. (In fact, one alternative, where it is necessary to be particularly cautious about distortion of the existing structure, is to artificially reduce the harmonic constants (i.e. the constants which relate distortion to restoring force) of the existing structure to less than their true value, and assess distortions under that assumption.) In this class of embodiments, the freedom allowed in the existing structure permits more accurate assessment of contributions from hydrogen bonding to the existing structure, or salt bridge formation with the existing structure. Again, the computational burden at run-time is decreased by maintaining relevant variational parameters (i.e. parameters which show energetic dependence on incremental changes) for the already determined structural groups). This means that optimization steps needed as material is added are simplified.

CUSTOMIZED COMPLEMENTARITY

Some further embodiments of the invention permit customization of structure to complement a known structure. For example, instead of starting (as in the presently preferred embodiment) with a known structure onto which new structure will be added, these classes of embodiments will use a map of a known structure as one of the preconditions for definition of the new structure, but at least some of the predefined structure will not be a part of the structure as manufactured.

For example, this provides one way to tailor the specificity of antibodies: the known conformation of an immuno-determinant group on the surface of the target antigen (positioned (at least for an initial hypothesis) at a distance from the body of the antibody which is generally typical for the binding action of antibodies of the type being constructed) can be used as part of the starting conditions, and the CDR loops can be custom-built (using the innovative methods disclosed herein) for a good complementary fit to the immuno-determinant group on the surface of the desired antigen. (It is believed that customization of CDR loops for complementarity to a known antigen conformation has been suggested, but the innovative methods disclosed herein provide substantial advantages in performing this.)

Specifically, cofactors and inhibitors are very important keys to the operation of many enzymes. These may be regarded as key elements in biological "logic": the availability of multiple-input logic gates is essential to construction of complex logic, and enzymes which have multiple "inputs" (i.e. which have cofactor or inhibitor sensitivities) are a very important part of this necessary capability. To continue the analogy with electronic systems, the cofactor and inhibitor sensitivity of enzymes may be thought of as providing an "entry point" into the programming which is built into the existing biological structure. That is, modification of the cofactor and inhibitor sensitivity provides one way to modify the biological programming.

Thus, one important class of embodiments uses a map of a known enzyme structure as one part of the initial conditions; uses a map of the known conformation and structure of a desired cofactor or inhibitor (positioned in the spatial relationship to the enzyme's receptor site characteristic of active cofactors or inhibitors achieving functional activity at that site) as another part of the initial conditions; and reconstructs, by the innovative methods disclosed herein, the portions of the enzyme structure nearest the receptor site to modify the enzyme functionality.

Such methods can be used not only to produce an enzyme to fit a cofactor (or inhibitor); they can also be used to produce a cofactor (or inhibitor) to fit an enzyme. Again, the known conformation of the complementary structure (in this case the enzyme structure, at least in the neighborhood of its receptor site) is used as a starting point, and the desired structure is tailored (using the methods of the present invention) for complementarity.

In tailoring enzyme structure generally, an important consideration is that the energy transfer mechanisms (and, in many cases, the structural flexibility) in the starting enzyme structure must be preserved. This can provide constraints on the location where additional structure is added. This additional complexity of enzymes also means that the incremental construction methods of the present invention are particularly advantageous: the dynamics of enzyme structure and functionality can be very complex, so that the ability to do incremental modification of an existing structure, without having to totally understand and reconstruct the existing structure, is potentially very useful.

The methods of the present invention could also be applied to designing specific "poisons", i.e. structures which would fit an enzyme active site and form covalent bonds to stop the functioning of the enzyme. If the conformation of the enzyme's active site were known, the innovative techniques disclosed could be used to provide an enzyme poison which was specific to that enzyme only. (The same technique could be applied to other receptors of many kinds.) This would permit specific targeting of enzyme operations which it was desired to disrupt. This capability could be useful for therapeutic uses and also for pesticides.

Other classes of embodiments permit polypeptide chains to be constructed for complementarity with other types of macromolecules and for other reasons. For example, antigen tailoring is another extremely useful area of application: tailoring of small custom proteins to mimic characteristic conformations of virus coats would provide an immensely valuable capability to generate safe vaccines against a wide variety of viral diseases.

Another useful area of application is for anti-idiotypic antibodies. (Anti-idiotypic antibodies are antibodies which selectively detect the presence of antibodies of a given specificity.) Using the innovative methods disclosed herein, proteins can be manufactured to mimic the activity of anti-idiotypic antibodies, and can therefore be used as very sensitive and selective diagnostic tools.

For another example, the present invention also permits hormones to be customized for complementarity with a known receptor site conformation. While hormones are often relatively short polypeptide chains (e.g. 40 amino acid residues) which may not fold spontaneously into stable domains, the interaction of the hormone with the receptor site does involve an extended fit, and the innovative methods disclosed can be used to design hormone sequences for optimal fit to any known receptor site. This is particularly advantageous in the area of drug design, since it means that drugs can be designed and manufactured, according to the innovative teachings of the present application, to fit a certain receptor site more selectively. This means that the chance of side effects and/or generalized toxicity can be reduced, while the desired efficacy of the drug is increased.

For another example, the innovations disclosed herein also permit simulations of virus receptor sites to be customized and manufactured. Viruses will normally attack cells by binding preferentially to a specific site on the cell surface (known as the "virus receptor" site). If the conformation and sequence of the binding region of the virus is known (and, preferably, if the conformation and sequence of the receptor site on the cell wall is also known), the innovative methods disclosed herein can be used to create a manufacturable structure which is complementary to the virus active site, i.e. which simulates the virus receptor site on the cell wall. (The therapeutic advantage of this is that each simulated virus receptor site can take an active virus particle out of circulation, by "decoying" the virus particle into releasing its nucleic material in a location where no propagation can occur. Since the decoy receptor site structure largely simulates a native conformation, it has low chances of inducing antigen activity.) In this class of applications, the innovative methods for more radical reconstruction can advantageously be applied: the decoy receptor structure does not necessarily have to replicate the full area of the cell wall domain, but only so much of it as will suffice to bind the virus. Moreover, the decoy receptor structure does not have to replicate the structures which permit cell wall domains to combine together stably, nor does it have to replicate structure relevant to the internal interface of the cell wall. Thus, the structure of the cell wall domain (which typically will be a glycoprotein) can optionally be substantially truncated in designing the decoy receptor structure.

The innovative methods disclosed could also be applied to situations where it was desired to add non-peptide structure. The key to such applications generally is the ability to define a set of "building blocks" which is large enough to be useful (in the context of whatever problem is being solved), but which is small enough to be not overwhelming in storage and computational demands. For example, one optional application would be to customize the carbohydrate portion of glycoproteins, by including a modest set of oligosaccharide blocks in the library.

For example, a set of common monosaccharides (e.g. the six most common hexoses plus fucose, and/or triplet blocks containing sequences of these) can also be used as library blocks. In embodiments where the library is allowed to contain heterogenous blocks—e.g. where the library contains both oligosaccharides and oligopeptides—appropriate penalties should be added into the figure of merit calculations, so that the optimization process will not introduce disfavored heterosequences unnecessarily. Moreover, the transition blocks should also be included in the library, if construction across the transition region may be desired. For example, glycoproteins require one of two specific links ("O-links" at serine, or "N-links" at asparagine) at the peptide-saccharide transition, as is well known to those skilled in the art.) Adjacent monosaccharides can have steric hindrance constraints, so that the advantages of storing oligopeptides as library blocks are also partly applicable to oligosaccharides (if glycoprotein or polysaccharide construction is desired).

The expressed and refolded single chain binding proteins of the invention can be labelled with detectable labels such as radioactive atoms, enzymes, biotin/avidin labels, chromophores, chemiluminescent labels, and the like for carrying out standard immunodiagnostic procedures. These procedures include competitive and immunometric (or sandwich) assays. These assays can be utilized for the detection of antigens in diagnostic samples. In competitive and/or sandwich assays, the binding proteins of the invention can also be immobilized on such insoluble solid phases as beads, test tubes, or other polymeric materials.

For imaging procedures, the binding molecules of the invention can be labelled with opacifying agents, such as NMR contrasting agents or X-ray contrasting agents. Methods of binding, labelling or imaging agents to proteins as ell as binding the proteins to insoluble solid phases are well known in the art. The refolded protein can also be used for therapy when labeled or coupled to enzymes or toxins, and for purification of products, especially those produced by the biotechnology industry. The proteins can also be used in biosensors.

BRIEF DESCRIPTION OF THE DRAWINGS

The present invention will be described with reference to the accompanying drawings, wherein.

DESCRIPTION OF THE PREFERRED EMBODIMENTS

Sample preferred embodiments of the present invention will now be described. However, it should be noted that a very wide variety of modifications and variations is believed to be possible. A number of those modifications and variations are specifically discussed below to illustrate some of the breadth of application of the innovative concepts disclosed. However, it is believed that the multiple inventions presented in the present application are collectively (and in some cases individually) of truly pioneering scope. Therefore, it is impossible to predict all of the technological contexts in which the present inventions may be advantageously applied in the future. The numerous suggested applications are therefore not to be taken as exclusive, but merely as suggesting particular contexts where the present inventions may be advantageously applied.

OVERALL ORGANIZATION OF THE METHOD

Figure 1:
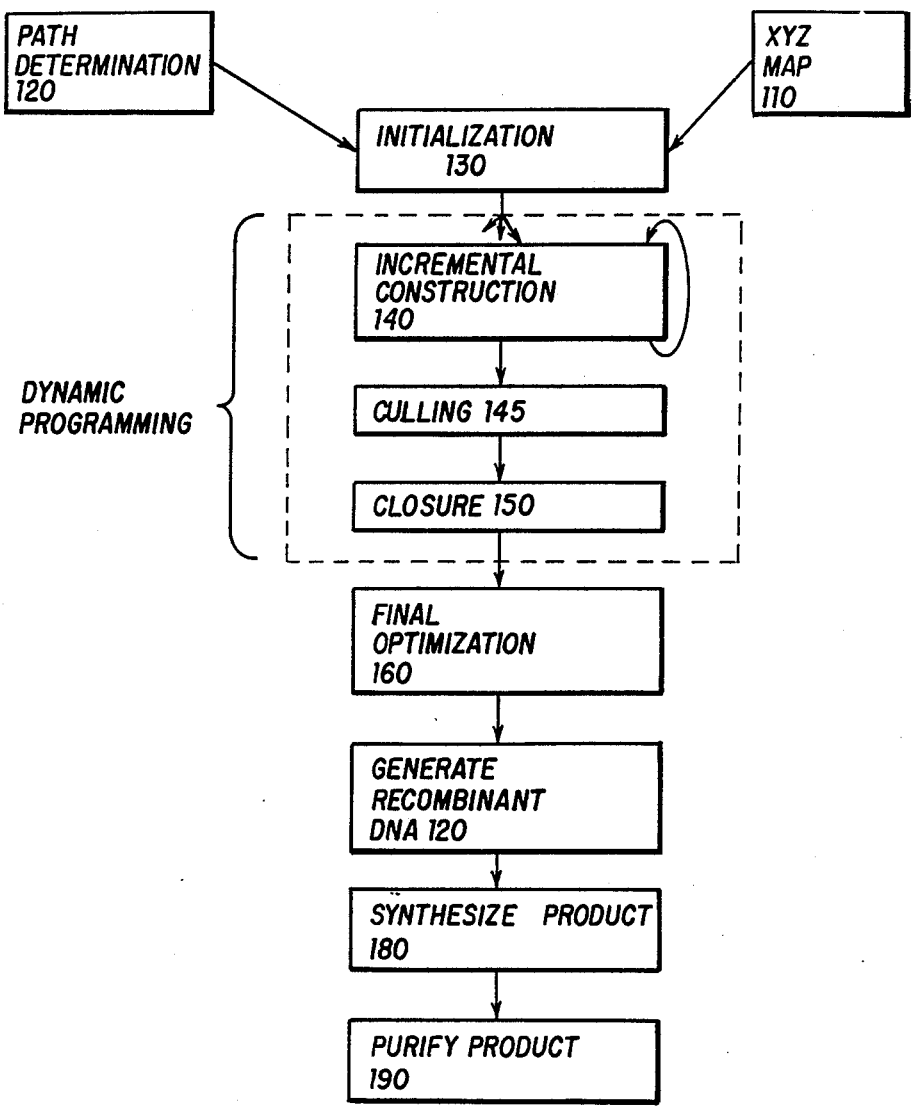
FIG. 1 is an overview of the main steps in the method of the present invention.

FIG. 1 shows the overall structure of an innovative method for modifying or building onto a polypeptide structure, according to the present invention. Block 110 indicates that the starting position is a map of multiple parameters in an XYZ coordinate space. The units used in this coordinate space preferably correspond to the real experimentally determined dimensions of a chemical structure which is desired to be modified. A tremendous variety of such structures is known to those skilled in the art, and, as the art of protein engineering and protein structure analysis continues to advance, it may be expected that a further increasing number of such structures will come to be known.

In the presently preferred embodiment, the starting structure is the Fv portion of an antibody, consisting of a so-called "variable light" ($V_L$) domain and a "variable heavy" ($V_H$) domain held together by non-covalent interactions. As is well known in the art, this basic structure can further be modified by appropriate selection of the hypervariable loops (also known as CDRs, or complementarity determining regions).

However, the XYZ map 110 preferably used as the starting point contains much more information than merely that shown in a simple representation of its backbone. Preferably, as will be discussed below, this map contains information equivalent to a representation along the surface of the predetermined structure, or at least along the portion of the surface which is sought to be modified, which includes localized electrostatic charge, electric field dipole moments, localized propensities to form the donor or acceptor half of a hydrogen bond, and optionally other factors as will be discussed below.

The generalized path determination 120 is preferably made, at least in the principal preferred embodiment, by a human operator. That is, as discussed above, an objective is defined for the expert system. Together with a general starting point and general ending point, some general indication of a path between the starting and ending points may optionally be predefined for the expert system.

The first step in the incremental construction process is an initialization step 130. In general, the task at this point is to format the preconditions in such fashion that the incremental construction step 140 can begin its operation. The incremental construction step 140 is then performed iteratively until the chain is almost finished, at which time a closure step 150 is used to finish the process. A tweaking step 160 is then preferably used to further optimize the solution thus derived. The result of step 160 will be a three-dimensional polypeptide structure which contains peptide residue sequence information, in addition to a great deal more information. The residue sequence information is then used as input to a conventional step 170, wherein recombinant DNA is generated according to this polypeptide sequence. (As is well known to those skilled in the art, any peptide sequence (of natural amino acids) can be encoded as a sequence of nucleotide triplets.) Thus, the DNA molecule generated in accordance with the peptide sequence information is joined with sequences that allow it to be expressed into the desired peptide (protein) product, and is transformed into an appropriate host (such as *E. coli, B subtilis,* or a higher organism) by standard means. The transformed strain is grown in such a way that it will synthesize the protein product (step 180), and the product is then purified by conventional methods (step 190). Thus, substantial quantities of the specified protein can readily be manufactured.

XYZ MAP OF EXISTING STRUCTURE

Figure 2:
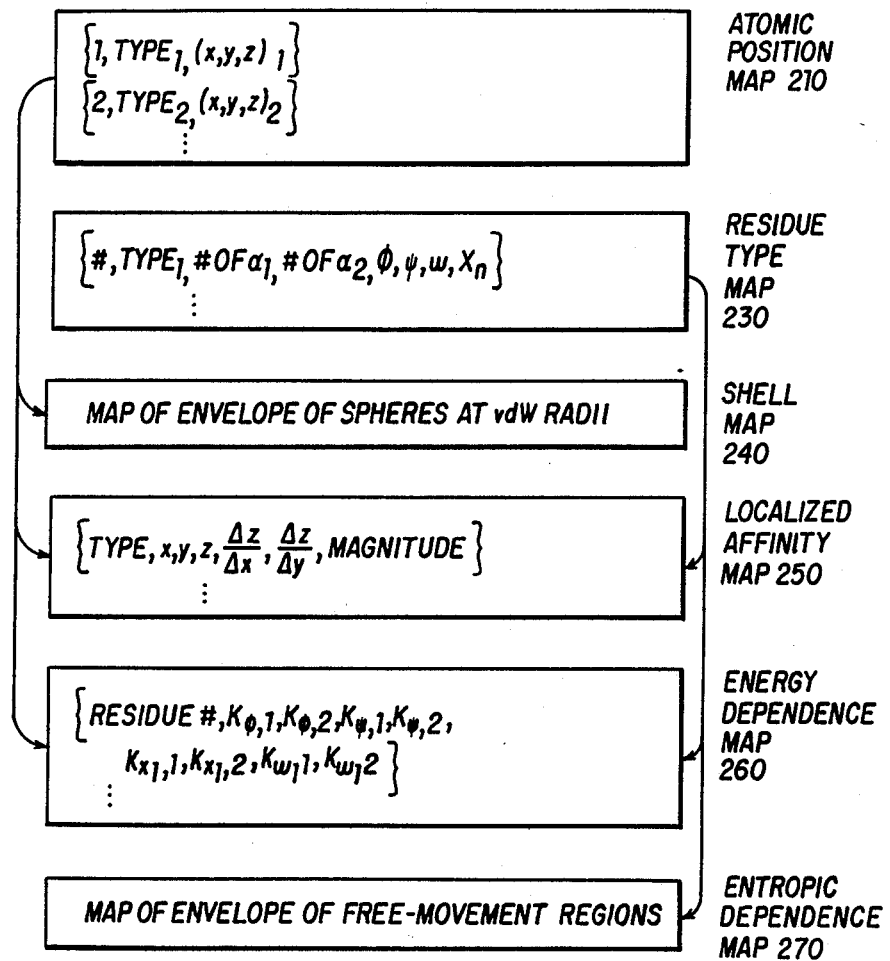
FIG. 2 shows the main elements used in the XYZ map 110 in the presently preferred embodiment, and also indicates some of the sequence preferably used to derive any elements which are not initially available.

FIG. 2 shows a sample of the specification of the XYZ map 110, together with the steps used to generate any portion of the desired specification which is not initially available. This "map" is preferably a data structure which contains a mapping of many attributes of interest onto a spatial representation (e.g. a Cartesian coordinate system for the neighborhood where a linker is desired to be constructed.)

ATOMIC POSITION MAP

The atomic position map 210 provides a bare-bones starting input. This may optionally contain no more than a list of atomic types and positions. Such lists, while they may be extensive data structures, are readily available in standard format. For example, the protein data base, created and supplemented by the Brookhaven National Laboratory in Upton, Long Island, N.Y. (called the Brookhaven Protein Data Bank (BPDB)) has a number of such specifications for protein structures. For purposes of the present invention, the defined orientation and XYZ position of this specification is arbitrary. This standard-format information provides a low-level starting point from which additional information is preferably now generated. Of course, if additional information is available as a starting point, it is not necessary to generate all of it.

RESIDUE TYPE MAP

The initial data is preferably manipulated to derive a residue type map, if this information is not already available. For each peptide link (amino acid residue), this map 230 preferably contains a unique number which identifies the sequence of the residues, a type designator (indicating whether the residue here is glycine, tryptophan, or whatever), XYZ components for the starting and ending alpha carbons of the chain, and psi values for this particular peptide block, as well as an omega value (corresponding to torsion around the backbone of the peptide block), and one or more chi parameters indicating values of the side chains at this block. (For example, glycine has no chi parameters, since there are no degrees of freedom, and histidine has two degrees of freedom. That is, (1) the aromatic ring structure (which must remain coplanar) can be rotated, within constraints, around the axis from a beta carbon to the gamma carbon, and (2) the side chain can also rotate within constraints around the axis from the beta carbon to the alpha carbon.)

Alternatively, it may also be desired to carry XYZ coordinates (and/or pointers to the atomic position map 210) for all of the atoms in the side chain. In either case, a fully sufficient set of information is provided; the difference is only in how that information is to be formatted. Similarly, the alpha carbons, instead of being specified by XYZ coordinates as just mentioned, may instead be positioned by pointers into unique atom numbers in the atomic position map 210.

The derived angles presented in the residue type map 230 are readily derived by well known procedures from the atomic position map 210. However, in many cases, it may also be possible to provide the information in the residue type map 230 as input data.

In the presently preferred embodiment, the information in atomic position map 210 and residue type map 230 is now used to generate a localized affinity map 250.

SHELL MAP

A further transformation step is to use the atomic position map 210 to generate a shell map 240. That is, the atomic type and XYZ coordinates. The atomic position map 210 can be directly transformed, using van der Waals radii for given atomic types, into a shell map 240. Preferably the minimum van der Waals radii are used, since the derived shell map 240 will be used to initially exclude hypothesis (in the presently preferred embodiment). That is, this shell map 240 specifies a derived shell outline. The atomic positions in 210 are transformed into spherical surfaces, and conventional hidden-surface graphics methods are then used to derive the shell map 240. The shell map 240 represents a boundary for existing structure. Preferably, a simple algorithm is used to define this map, since portions of this map will frequently be regenerated as the incremental structure proceeds.

LOCALIZED AFFINITY MAP

A localized affinity map 250 is now generated from the atomic map 210 and residue type map 230. This localized affinity map 250 is also a list which contains, for each item, a type specifier, XYZ coordinates, a magnitude specifier, and a direction specifier. The type specifier can preferably be a specifier of fixed charge, dipole, hydrogen-bond propensity index, and (optionally) disulfide-bond propensity index. The magnitude parameter permits the amount of a fractional fixed charge to be specified, or permits the magnitude of a dipole moment to be specified. The magnitude is preferably permitted to be a signed value, so that hydrogen donor propensity or hydrogen acceptor propensity is indicated by the sign bit in this field. However, of course, this could simply be shown by including hydrogen donors and hydrogen acceptors separately in a type field instead. The direction field requires two parameters; in the present preferred embodiment the Z over X and Z over Y ratios are arbitrarily used to specify this, but of course other geometric indices could be used instead.

ENERGY DEPENDENCE MAP

The residue type map 230 and localized affinity map 250 are now used to generate an energy dependence map 260. This energy dependence map contains pointers to the atomic position map 210, and specifies, for each of the angle parameters carried in the residue type map 230, an estimation function. The estimation function can be (e.g.) a second order approximation for estimating dependence of energy on the angle parameters, optionally combined with a sine function or second order polynomial of opposite leading sign, for smoothly bridging saddle points. Alternatively, this energy dependence map could be stated as a dependence for atomic number and XYZ coordinates, or these additional $E(X,Y,Z)$ parameters could be stored in addition to the $E(\phi,\text{psi}, \ldots )$ parameters. However, modeling energy dependence for variations to existing structure in terms of structural angles is believed to be more advantageous, since it permits more direct provision of high-level results.

It should be noted that the generation of a shell map 240 from an atomic position map 210 is already performed by readily available 3-dimensional graphic tools used for displaying protein structures, such as "Frodo." See the article by T. A. Jones at 11 *J. Appl. Crystallography* 268 (1978).

ENTROPIC DEPENDENCE MAP

Finally, in the presently preferred embodiment, an entropic dependence map 270 is preferably derived from the atomic position map 210, the residue type map 230, the localized affinity map 250, the shell map 240, and the energy dependence map 260. The entropic dependence map is preferably encoded as an additional shell map, formatted similarly to the shell map 240, which shows "soft" shell regions, on the surface only of the predetermined structure, wherein significant entropic components are defined by delocalized atomic groups. For example, the epsilon amino group of a surface lysine residue will typically not be spatially determined, and there will be a significant entropic contribution due to the freedom of movement of this terminal sidechain group.

SEQUENCE OF GENERATING XYZ MAP

It should be noted that the sequence of steps in deriving this information is arbitrary. A primary teaching is that a high level XYZ map should be used as a starting point, and it will be obvious to those skilled in the art of computer simulation and/or computer graphics that a tremendous variety of formatting options exist in the representations used to encode the information in this map. Moreover, a large variety of different processing steps can be used sequentially to derive the needed information and the needed format.

There also exists a substantial scope of alternatives as to what specific information is used in the map. For example, in the presently preferred embodiment, disulfide bonding of the additional structure is not permitted. This is because the disulfide bonding is normally used relatively sparingly in nature, and adding disulfide bonding presents substantial risks of creating inappropriate disulfide bonding. (Multiple disulfide bonding is more commonly used in relatively large protein structures, and in vitro it can be observed that some such structures fold only with difficulty.)

For another example, the use of entropic dependence map 270 is also very much an optional step; part of the advantages which could be obtained by optimization using this map can be had simply using expert rules appropriately. That is, a significant teaching of the present invention is that localized non-spatial parameters should preferably be used in the starting map (and those skilled in the art will readily recognize the relevance of at least some of those non-spatial parameters to the optimization process), but those skilled in the art will also recognize that not all of these non-spatial parameters must be considered for every construction which might be performed.

It should also be recognized that many of the data transformations used will dovetail closely with the graphics formatting used in the presently preferred expert assistant embodiments. Many of the transformations specified in the foregoing examples are those which would be used in any case in making a three-dimensional graphics simulation of a protein structure. Many others will provide very convenient input for a graphics display. For example, localized charge can be overlaid on a graphics display as an additional mapped color, to show location, intensity, and sign of localized charge. Similarly, dipole moment can be mapped onto a three-dimensional graphics display as short line segments of a distinctive color, whose length is proportional to the magnitude to the dipole moment and whose orientation indicates the orientation of the dipole moment. Similarly, hydrogen bonding acceptor or donor propensity can also be indicated by overlay color.

Thus, a spatial map containing a significant amount of derived overlay information is preferably provided as the first step. One advantage in providing a map which includes this overlaid high level information is that the necessary computation can be done beforehand, so that the expert decision making processing can run faster at a run time. This is particularly advantageous with the expert assistant class of embodiments, since the precomputation would be done as a batch job. While the precomputation of parameters may require relative extensive computation, this need only be done once, and the data thus derived can be stored with the predetermined structure in a library.

UPDATING THE XYZ MAP

It should also be noted that many of these precomputed parameters will be updated incrementally and locally as blocks are added. This is one advantage of the particular data structure given that precomputation of these parameters can be performed locally, by accessing and updating individual items in a list, rather than having to do global recomputations.

SPATIAL PARTITIONING

A second preferred feature in the data structure is the partition of the volume of space addressed. That is, the XYZ volume being manipulated is preferably divided into cubes, by partitioning on each of the Coordinate axes. (However, of course other space filling partitions could be used instead, or overlapping partitions could be used.) The advantage of this is that many of the operations which are spatially limited can be performed by calculation only over a relative small volume. For example, a partition into cubes which are ten Ångstroms on the side are used, a search through all cubes which are adjacent into the volume of interest is guaranteed to discover all possibly relevant candidates for hydrogen bonding and most other interactions of interest; electrostatic interactions (salt bridge formation) may be significant at distances up to about 15 Ångstroms, so optionally next-nearest-neighbor cubes would provide additional assurance of finding all salt bridge candidates. That is, this partitioning permits various search strategies to be rapidly implemented locally, which further facilitates incremental construction and use of sophisticated optimization strategies.

Once the XYZ map has been initially defined, the first step will be an initialization step 130. However, for clearer exposition, the incremental construction step 140 will be described first, and the initialization step 130 will be described after that, out of sequence.

LIBRARY BUILDING BLOCKS

In the presently preferred embodiment, the library contains blocks of usefully small size with multiple precalculated parameters stored for each block. That is, in the presently preferred embodiment, the library includes a complete list of tripeptide sequences. The number of such sequences is 8000.

Alternatively, a different block size, such as dipeptides or tetrapeptides, could be used in the library. This choice depends on several factors, including the tradeoff between run-time computing burden and the number of parameters which must be stored. However, in any case, it is preferred that the size of the blocks in the library include a full set of blocks of the length of tetrapeptides or shorter.

Optionally, the library may contain blocks of varying lengths. For example, a tripeptide library could be supplemented with tetrapeptides, or with a selection of experimentally determined substructures (together with their experimentally determined conformation parameters).

For each block in the library, stored parameters preferably include:

(1) All local minimum energy conformations for each block. For a tripeptide library, this would include at least one parameter set ($\phi_1$, psi$_1$, $\phi_2$, psi$_2$). Depending on the residues in the particular tripeptide block, it might also include minimum-energy side chain angle conformations for each of the minimum energy conformations, so that chi$_{1,1}$ (the chi$_1$ angle of the first residue), chi$_{2,1}$ and/or chi$_{3,1}$ would also be specified. Optionally and less preferably, chi$_2$ values could also be specified for some residues.

(2) Moreover, the dependence of energy on these various parameters in proximity to each of the local minima must also be stored. That is, together with each of the local minima, an approximation which will permit estimation of the energy for parameter values slightly different from these minima is preferably used. Preferably, these estimations are second order in each of the parameters separately, without cross terms. That is, for a given local energy minimum (for example, for the alpha$_L$ local minimum in each $\phi$, psi pair) parameters would be stored corresponding to an estimation polynomial:

$$E(\phi, psi) = E(\phi_0, psi_0)$$
$$+ K_{(\phi,1)}(\phi - \phi_0) + K_{(\phi,2)}(\phi - \phi_0)^2$$
$$+ K_{(psi,1)}(psi - psi_0) + K_{(psi,2)}(psi - psi_0)^2,$$

where $\phi_0$ and $psi_0$ are the ($\phi$,psi) pair for the local minimum, and E is estimated energy contribution (figure of merit component).

Such a second-order fitting technique is particularly suited for parameters where the local energy minimum is relatively sharp. However, other convenient fitting methods may be used for areas where a relatively broad range of values may have to be considered. For example, in the conventional Ramachandran plot, there is a region between the right-handed alpha and the beta sheet local minima which is energetically significantly disfavored, but not entirely forbidden. In estimating possible energies over such a region, the energy may be locally estimated, for example, as the minimum of three terms, where two of the terms correspond to second-order energy estimates at the two local minima, and the third term represents, for example, a sine-function (or a second-order function of opposite leading sign) which helps provide smoothly varying estimates near the maximum disfavored point. That is, piecing together the estimate may be done using a sine function to give a smooth local approximation at the saddle point. Of course, alternatively, a wide variety of other conventionally known ways to piece together an estimation function may be used.

Thus, when a block is retrieved from the library, its possible local minimum energy conformations are retrieved with it, but the parameters to do estimation for modifications of the initial hypothesis are also retrieved with it. Thus, optimization can be done online without full recalculation of all of the relevant contributions, by exploiting prestorage of dependencies in this fashion.

Moreover, each of the blocks in the library preferably includes additional parameters which can be used as input to expert rules. For example, a one-bit logical (or few-bit integer) parameter can be prestored to indicate whether a given block is hydrophobic or hydrophilic.

For another example, a net favorability parameter can also be prestored with each block. That is, some tripeptide sequences can be considered initially to be regarded as more favorable than others. For example, a glycine-glycine-glycine sequence may be disfavored, because it provides a negative entropic contribution to the kinetics of folding the protein domain.

In addition, localization parameters are preferably also prestored. Prestorage of these facilitates calculation of some of the contributions due to interaction between multiple residue groups. For example, for each residue in the block a pK value for the side chain is preferably stored. (This parameter, in essence, indicates propensity of the side chain to ionize, and thus provide a localized electric charge, at different ambient pH values.) In addition, XYZ coordinates for an estimated equivalent position for the ionized charge (or equivalent partial charge), if any, is also stored. This means that electrostatic calculations can be used to measure the energy contribution due to formation of salt bridges.

Similarly, van der Waals radius parameters may be stored separately for each of the atoms in the side chains. (Alternatively, these radii may simply be calculated by direct lookup for the various types of atoms (carbon, oxygen, sulfur, hydrogen, nitrogen) at run time.)

Similarly, an electric dipole moment vector, (including position, orientation and magnitude) is also preferably stored for each side chain. Again, precomputation of this parameter permits it to be readily transformed, for different conformation values, to permit ready computation of van der Waals force contributions to bonding energy and also ready optimization of dihedral angle parameters and side chain angle parameters to optimize the van der Waals force contributions.

Similarly, localized hydrogen bonding propensity values are also preferably stored. That is, for each side chain in the blocks in the library, there will be some sites (such as the delta-1 nitrogen in histidine) which have a propensity to form the donor half of a hydrogen bond, and there will be other sites (such as the epsilon-2 nitrogen in histidine) which have a propensity to be hydrogen acceptor sites. Thus, the building blocks in the library will each have precomputed donor and acceptor locations. Note that these donor and acceptor locations will include some locations in the main chain, i.e., in the peptide backbone. Normally, the oxygen in the peptide chain can act as a hydrogen acceptor, and the amide group in the peptide backbone can act as a hydrogen donor. For example, in beta sheet structures these two sites will bond together extensively in a distributed fashion. Note that estimation of hydrogen donor and acceptor locations is a function of the particular block in the library. For example, a nitrogen donor in one side chain may have a strong propensity to form a hydrogen bond with a hydrogen acceptor in an adjacent side chain. Thus, precalculation of this parameter, and storage of XYZ positions, together with coefficients for rotational transformations of those XYZ positions in terms of the angles which might be modified, greatly expedites the computational process at run-time.

These parameters may have to be adjusted for proximity effects; for example, if there are two donor sites in proximity to a single acceptor site, the propensity value for that acceptor site will have to be adjusted. An advantage of the precomputation of parameters for library blocks, as taught in the preferred embodiment, is that such refined calculations can be done off-line (at least if the proximity effects are due to structures within the same oligopeptide block.

Moreover, entropic contributions, including steric hindrance contributions, can also be stored for multipeptide blocks in the library. Moreover, dependence of these contributions on the angles for this particular oligopeptide block can also be prestored. Thus, within a block in the library, the steric hindrance and unfavorable electrostatic interaction of two adjacent glutamate groups can be rapidly evaluated at run-time, since a simple polynomial and trigonometric calculation permits these contributions to be assessed based on the defined angle parameters.

LIBRARY BLOCK SIZE

The library contains blocks of usefully small size with multiple precalculated parameters stored for each block. In the presently preferred embodiment, the library includes a complete list of tripeptide sequences. The number of such basic sequences is 8000.

Alternatively, a different block size, such as dipeptides or tetrapeptides, could be used in the library. This choice depends on several factors, including the tradeoff between run-time computing burden and the number of parameters which must be stored. However, in any case, it is preferred that the size of the blocks in the library include a full set of blocks of the length of tetrapeptides or shorter.

OVERSIZED LIBRARY COMPONENTS

Optionally, the library may contain blocks of varying lengths. For example, a tripeptide library could be supplemented with tetrapeptides, or with a selection of experimentally determined sequences (together with their experimentally determined surface conformation parameters).

Thus, for instance, sequences and parameters (including conformation) could also be included in the library (by extraction from known structure specifications as they become available) for longer sequences, e.g. for sizes up through 8- or 10-peptide chains. In particular, substructures of specific functional relevance could be included. For example, one particularly useful element for tailoring antibody structures is known CDR loop structures. Another useful grouping is the 3 standard types of reverse turn configuration. Similarly, in alternative embodiments, strands of beta sheet, $\beta$-$\times$-$\beta$ fragments, alpha-helix pieces, or other larger substructures could also be used for library building blocks.

Preferably software-switchable search strategies are used, so that the user can specify a truncated search strategy. This capability means that automatic library updating can be set up as a self-sustaining process, without overburdening the library retrieval algorithms as the library expands.

INITIAL PATH SELECTION

Initially, the human operator preferably specifies a general path for the linkage. For example, in applications of the type discussed in the 902,970 application, where an Fv structure is to be simulated using a polypeptide single chain structure, one of the objectives will commonly be to stabilize the conformation of the two domains. Thus, the human operator will typically initially specify that the linker being constructed should run for a significant length along the joint between the two existing domain structures. In general, the general choice of initial path is a high enough level decision that the key question here is really what is the objective to be accomplished. That is, the general direction of the path is an objective which is preferably passed to the expert system and not a decision which the expert system is asked to make.

Thus, progress along the path originally selected is preferably strongly weighted in the hypothesis selection process. However, some flexibility is preferably allowed, to permit efficient deviations from the least-distance path to be found. (However, where a limited data set is being used for computational efficiency, of course hard limits need to be imposed on the regions for calculations are made.)

INCREMENTAL CONSTRUCTION STEP

The incremental construction will be described at a stage where a residue $L_{(N+1)}$ is being chosen and emplaced, in a situation where an existing structure, as well as a partially constructed additional structure up through residues $L_{N-1}$ and $L_N$ have been provided. Moreover, the XYZ parameter map is updated, at least locally, to correspond with the additional structure as it is inserted. (Thus, the additional computation at each incremental construction step is essentially the same. Nevertheless, joint optimization of multiple construction steps will eventually result, as will become clear below.)

RETRIEVE CANDIDATES FROM LIBRARY

Preferably, a set of multi-peptide building blocks is used to construct the polypeptide sequence one residue at a time. For example, when hypotheses for block $L_{(n+1)}$ are to be selected, blocks $L_{(n)}$ and $L_{(n-1)}$ can be used as indices to the library, to select the 20 triplets beginning with a pair of side chains which match the side chains defined for positions $L_{(n-1)}$ and $L_{(n)}$. Thus, use of multiple precomputed parameters for estimating dependences in the library permits rapid adaptation of the next residue in combination with the values of the previous residues and with the XYZ environment of the residue.

The described example will assume that the library called on is a library of tripeptide blocks. However, other library configurations can be used instead. The choice of library format will be discussed in greater detail below.

Thus a fast look-up operation in the library will define a set of candidates for $L_{(N+1)}$. That is, in the example using the library of tripeptide blocks, a data set of all blocks for the type $(L_{(N-1)}, L_N, *)$ will be retrieved from the library, where * represents a wild card character, i.e., any block in the library which matches the other parameters will be retrieved. This step is shown as block 310 in the flowchart of FIG. 3, and the result of this block is a candidate set.

The search for legal blocks 310 identifies a candidate set of blocks in the library 305. Preferably the candidates from the library 305 come with three computed parameters, such as spatial shell parameters, generally corresponding to those show generally as XYZ map 110 in FIG. 1, and as data structures 210, 270 in FIG. 2.

The next step is shown separately here, but it is really a very simple step: the parameter values which were retrieved from library 305 for each of the candidates are now translated, in accordance with the location of $L_N$ and the orientation of $L_N$ with respect to $L_{N-1}$, so that the stored parameter values are in the same frame of reference as the XYZ map 110. This provides a set 325, which is a set of candidates $C_K$ together with parameters which have been mapped into the appropriate coordinate set.

A further step, which provides the advantages of pH-dependent customization, is to modify the parameters stored with the candidate blocks in accordance with the characteristics of the predetermined environment in which the end-product structure is desired to operate. One aspect of this is that, as discussed elsewhere, pK parameters are converted into localized fractional charge values. Another aspect is that other environmental parameters can also be used to modify stored values. For example, some of the hydration contributions may be affected by diluents in an aqueous environment (e.g. by significant concentrations of salts). Other constants may be affected by the target operating temperature range.

SPATIAL INTERFERENCE CHECK

The first candidate selection operation—preferably a spatial interference check 340—is now performed. This spatial interference check uses the shell map 240 as a test for compatibility of each of the candidate residues $L_{N+1}$.

More precisely, in the presently preferred embodiment, the spatial interference check 340 is performed in two branches. First, if neither of the residues $L_{(N-1)}$ or $L_N$ is glycine, a threshold is placed on spatial interference measures: if neither of the preceding groups is glycine, and if the space-filling parameters for the candidate block including group $L_{N+1}$ interpenetrates with the shell map 240 for more than a predetermined threshold depth or over an area larger than a predetermined threshold area, the candidate is excluded.

One sample way to determine this is to use an iterative process which starts from the XYZ atomic positions of the last group $L_{N+1}$ and marches outward for the appropriate van der Waals radius from each atom. If interference is found at the central XYZ location of an atom (or at least of certain atoms) (such as the backbone and carbon data atoms) the hypothesis is rejected out of hand if interference is found inside the minimum van der Waals radius, or at the location of certain other atoms (such as the epsilon amino nitrogen of lysine) which have a relatively large freedom of movement, then the hypothesis will be retained, to be reexamined as described below during the candidate adjustment step.

Optionally, the spatial interference check 340 can be performed using a variety of other known algorithms, many of them derived from computer graphics representations. See generally, for example, the review articles in the July 23, 1987 issue of *Electronics*, which are hereby incorporated by reference. Thus, it will be understood that the specific example of how to perform this spatial interference check given below is provided merely as one illustrative example.

CHARGE AND SALT BRIDGE CHECK

In the presently preferred embodiment, this is a salt bridge check 330. This check performs a quick integration check on the volume where residues $L_{N+1}$ is expected to be located, and on surrounding blocks. This quick check is used to exclude some candidates. If an electric potential which is above a certain threshold is found in the region where the $L_{N+1}$ residue is thought to be located, all candidates with more than a certain threshold value of localized charge of that same sign are excluded. Moreover, nonpolar candidates are excluded. Since this check can be performed very rapidly with minimal computation and infrequent necessity for backtracking, it is preferably performed.

HYDROGEN BONDING CHECK

In the presently preferred embodiment, the next step performed is a check for hydrogen bonding. That is, in the hydrogen-bonding-check step 350 any candidate in which two successive residues are not hydrogen bonded is strongly dispreferred, and such candidates are thrown out if other candidates are available.

This step, like the salt bridge check 330, preferably refers to the local affinities map 250.

MERIT SELECTION STEP

The next step is a rule-based merit selection step, which performs ranking and culling of the candidates based on some rule-based expert decisions, plus, for the first time, some numerical calculation of figures of merit. That is, at this stage a rough figure of merit will be computed for at least some of the remaining candidates. Conditional exclusion rules are preferably used at this stage. That is, if five candidates can be found which have a rough figure of merit above the threshold for this stage, all groups which have (for example) an outward-facing hydrophobic residue will be excluded. Moreover, this stage includes partial flexibility in the candidates, but not as much as will later be introduced. That is, for example, the energy-dependence values for the dihedral angles may be used to modify each of the hypothesis to introduce alternative hypothesis wherein each dihedral angle parameter is separately tested, in three discrete steps by introducing variations in each direction of the amount corresponding to one-half kilocalories per mole unfavorably energy contribution, based on the precalculated parameters. Preferably these variations are done sequentially, and only the most favorable of them is retained. Thus, for example, using tripeptide blocks, $\phi_1$ may be specified by the look-up table to have a value of 85° in the candidate hypothesis being considered. The energy dependence parameters also stored may indicate (for example) that a one-half kilocalorie per mole unfavorable energy variation would result if this parameter were changed by 10°. Therefore, in addition to evaluating the candidate hypothesis, the additional hypotheses where $\phi_1$ was 75° and 95° would be evaluated.

Next parameters $psi_1$, $\phi_2$, and $psi_2$ are sequentially tweaked similarly. Since these alterations are preferably performed sequentially rather than combinatorially, the number of additional checking steps is relatively small, at least in relation to the solution space which is mapped out. That is, this rough selection performs a quick check to see if spatial interference rules or unfavorable electrostatic contributions can be eliminated, and it also performs a quick check to see if hydrogen bonding, salt bridge bonding, or van der Waals contributions can be obtained. Therefore, at this stage, very crude figure of merit rules are preferably applied to minimize the computation, since more detailed computation will be performed promptly. To expedite computation of such factors as hydrogen bonding contributions or salt bridge contributions, look-up tables can optionally be used rather than fully detailed maps. That is, optionally look-up tables can be used which implement rules such as, "proximity of a positive localized charge to a negative localized charge provides a favorable energetic contribution of ten kilocalorie per mole multiplied by the fractional value of each of the charges and divided by their distance in Ångstroms"; however, for a first approximation this rule can be implemented as a simplified rule which says, for example, that a partial charge will be estimated as providing a favorable energy contribution of 0.1 kilocalorie per mole if the charge is equivalent to more than 0.3 electrons of equivalent localized charge and if there is an uncompensated localized charge of opposite sign and of more than 0.3 equivalent partial charge within less than 7 Ångstroms of total offset (X difference + Y difference + Z difference) within the localized coordinate system being used, and that no contribution will be estimated otherwise.

Moreover, the crude estimation preferably performed at this step includes a test to make sure that the optimization process is not getting too far afield. Preferably the candidate set found is evaluated, and unless at least one candidate has shown a substantial favorable contribution or at least (for example) three candidates have shown a contribution above some lower threshold (for example a zero net contribution), the procedure will loop back to the earlier steps 330, 340, and 350, and reintroduce some of the hypotheses which were excluded at those steps.

CANDIDATE OPTIMIZATION

After the rule-based merit selection step 360 has been performed, a further reduced set of candidates will be passed to a candidate optimization block 370. At this point, a more detailed optimization of the candidates is preferably performed, together with a more precise evaluation of the energetic contributions of each.

Figure 4:
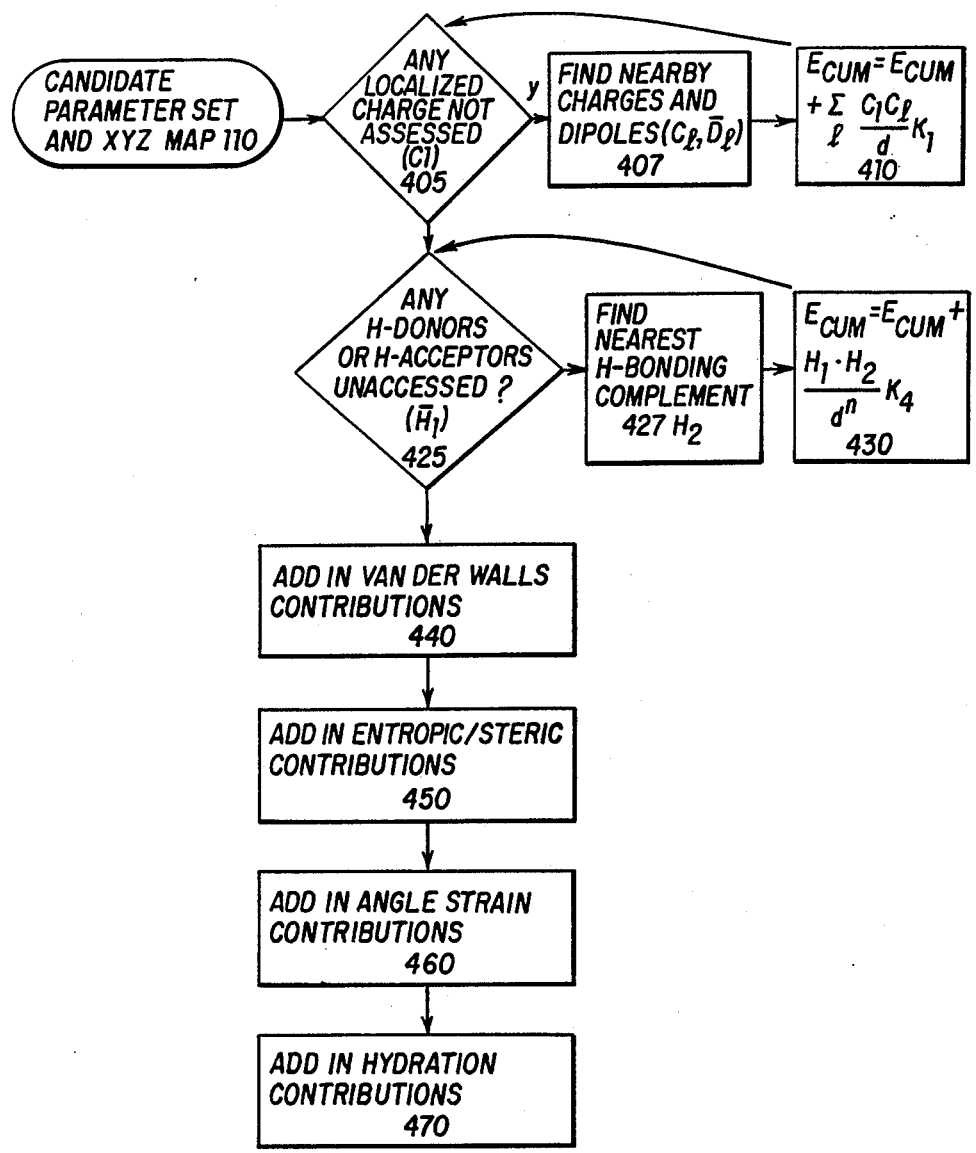
FIG. 4 shows steps which can be used in estimating net energetic contribution of a candidate for the next portion of a polypeptide structure being incrementally constructed.

FIG. 4 shows a sample procedure, as used in the presently preferred embodiment, to form an energetic estimate of any one particular conformation. Again, the example shown is merely one specific realization, and others could be chosen. It should be recognized that the sequence shown is not at all mandatory. Tests can be performed in various orders besides the specific order shown. Moreover, as shown by various examples of the foregoing and following discussions, some of the tests shown can be omitted, and numerous other tests could be added. (Most preferably software switches are used to enable some of the calculations to be omitted or curtailed, so that a partial and approximate estimation can be done quickly.)

It should also be recognized that the steps stated for estimating energy are useful not only to estimate energetic contributions to a figure of merit; they can also be used to find locally optimal conformations. Finding locally optimal conformations can be done by finding local minima in the energy estimates as conformational parameters are varied. That is, one simple procedure is to bracket the primary value of each parameter with alternative values, calculate the figure of merit for the alternative values, select one of the alternative values as the new primary value if it has a better figure of merit, and iterate this procedure until no further changes are made in one additional pass. Depending on the precision desired, multiple alternative hypotheses can be used. That is, for example, for each parameter $X_K$, the primary value $X_{K0}$ could be evaluated together with alternative hypotheses $X_{K1}$ and $X_{K2}$, which are equal to $X_K \pm 5°$, together with additional hypotheses $X_{K3}$ and $X_{K4}$, which are equal to $X_0 1°$. Alternatively, a smaller step size may be used after the first iteration has reached a steady state.

It should also be recognized that many other conventional methods for estimating energetic contributions from structure, and/or for finding the minimum-energy conformation of an approximately specified structure, can be used. For example, some programs for energy estimation of protein structure modifications which are believed to be available as of 1987 are CHARMM (discussed in the Bruccoleri article cited above), AMBER (see the Weiner et al. article at 106 J. Am. Chem. Soc. 765 (1984)), and DISCOVER (developed by Arnold Hagler et al.).

FIGURE-OF-MERIT ESTIMATION

In the sample flow of FIG. 4, the process by which an energetic estimate of a particular hypothesis is formed (e.g. for the purpose of performing step 380) will now be described in detail. It should be noted that a wide variety of computational shortcuts can be used to accelerate the estimation steps detailed below, and, as will be recognized by those skilled in the art of numerical computation, many shortcuts in addition to those specifically described can be used to implement the general functionality described.

In the following discussion, it should also be recognized that free energy may be used in some steps essentially as a figure of merit, and not as a precise scientific calculation. Therefore, it will be noted that in some of the following discussions artificial adjustments may be made to the "energy" figure which are not accurate, but which reflect the desired preference and dispreference weights allocated to various circumstances.

CONTRIBUTION FROM ELECTRIC POTENTIAL

First, the candidate parameter set is searched to see if there is any localized charge which has a magnitude greater than a certain level (for example 0.05 electron) and has not yet been assessed.

The reference to whether a parameter has been "assessed" in the following refers to a local tag bit which is preferably reset after each loop of estimation (FIG. 4 shows one loop of estimation), simply for bookkeeping during the estimation process. These tag bits may be carried as an additional bit within the parameter set of the localized affinity map 250.

Thus, blocks 4 and 5 search through all of element blocks contained in a candidate $L_{N+1}$, to see whether any localized charge value greater than the threshold is found. If so, a search is made for other localized charges which might be relevant to assessing the electrostatic energy contribution. In the presently preferred embodiment, this is done by searching all adjacent partitions in the XYZ map, and finding the nearest three charges within those adjacent blocks. This means that all possible charges within 10 Ångstroms of the candidate will be found, and no time will be wasted in assessing any possibly neighboring charge which is more than 20 Ångstroms away from the candidate position.

After the nearest three charges have been found, their energy contributions are summed. (Note that it may alternatively be preferable to simply sum over all charges found within an adjacent block, to avoid distorting the algorithm due to small partial charges which are close by, or alternatively the three charges which have the highest magnitude of charge to distance from the candidate region within the volume searched.

In any case, after the surrounding charge set has been selected, the energetic contribution of each is assessed, preferably using a formula such as $$E_{cum} = E_{cum} + K_1 C_1 C_2 d^{-1}$$

into the cumulative energy estimate $E_{cum}$, and the localized charge being considered is temporarily tagged as assessed. In the formula for energetic contribution due to electrostatic charge, the partial charge values $C_1$ and $C_2$ are allowed to be fractional in accordance with the well known relation between pK and propensity to ionize in a given environment. (A group will be 50% ionized at an ambient pH level which is equal to the characteristic pK for that group, and the degree of ionization varies therefrom in accordance with an exponential relationship.) The pK values for groups of primary interest are 3.9 for aspartate, 4.3 for glutamate, 6.6 for histidine, 10.1 for tyrosine, 10.5 for lysine, and 12.5 for arginine. Thus, depending on the ambient pH, it may or may not be appropriate to treat different groups as ionized. For example, aspartate will typically have a negative charge at blood pH, and will be neutralized only under extremely acid conditions.

Thus, both of the charge quantity values C1 and C2 may typically be fractional. K1 is preferably selected in units which are most convenient. In the present preferred embodiment, d is calculated in Ångstroms, and $K_1$ is preferably selected such that the energy results come out in the units of kilocalories per mole which are common and convenient in chemical thermodynamic calculations.

The energetic contribution made by introducing a localized charge is of course also dependent on the tensor of polarization. In the presently preferred embodiment, this is taken into account by again searching the neighboring boxes for dipoles, and adding in an energetic term proportional to the dot product between the incremental electric field $E_1$ and the dipole moment $D_N$ of each dipole:

$$E_{cum}=E_{cum}+K_3(E_1 D_N)$$

into the cumulative energy estimate $E_{cum}$, where again $K_3$ is selected for compatibility with the units preferably used. In this equation, $E_1$ is the calculated electric field vector component (localized to dipole $D_N$) due to the charge potential element $C_1$. Since $C_1$ is treated as localized at some location $(XYZ)_1$, calculation of the local electric field increment is straightforward.

It should be recognized that alternatively the effect of changing the environment could be accommodated by introducing a spatially varying parameter for local dielectric constant, which would take account of the difference between, for example, ambient aqueous environment and the density of hydrophobic groups often found in the interior of a protein domain.

Thus, at the conclusion of the evaluation operation 410, the localized charge which was being considered is now tagged as assessed. The test 405 is now reiterated, to see if there are any other new localized charges which have not been tagged as assessed. If there are any, again the search 407 for nearby charges and dipoles is performed, and the incremental energy modification 410 is repeated.

Alternatively, it would be possible to calculate the electrostatic potential terms using a distance-dependent permittivity term. As is well known, such a modification to Coulombic calculations can be useful in mimicking the polarization effect in attractive interactions, and in damping the longer-range interactions (which would be screened by solvent interactions in an aqueous environment).

Alternatively, it would be possible to calculate the foregoing energy terms using electric dipole terms. That is, instead of estimating a localized fractional fixed charge and using electrostatics to assess field contributions, one could alternatively estimate a localized fractional dipole, and assess the energetic factors by estimating dipole-dipole interactions. (Note that a dipole, corresponding to an oriented pair of opposing charges, is different from dipole moment, which represents a localized anisotropy in the polarization tensor.)

A further optional step (which is not used in the presently preferred embodiment) is to assess energetic contributions due to the introduction of localized dipole moments into areas where a substantial local electric field exists. This can be implemented, for example, as a test 415 which looks at the additional material to see if any dipole moment has been identified within the additional structure which has not been tagged as assessed. Similarly, if such a dipole moment is found, a volume search 417 is performed to find the local electric field. Thus, the cumulative energy estimate $E_{cum}$ can be updated for this hypothesis by adding in a contribution proportional to the dot product of the dipole moment being assessed with the local electric field.

As noted above, the figure-of-merit does not have to be a pure energetic computation. For example, fixed charges near the surface of a domain may be desirable to define binding or reaction pathways; and in such cases the energetic optimization should not be allowed to build in offsets to those desirable fixed charges. Therefore, in such cases, an additional term or condition is preferably added into the electrostatic estimations. For example, phantom opposite charges could be mapped into the XYZ map, near locations where fixed surface charges are desired for functional reasons.

HYDROGEN-BONDING PROPENSITIES

After the assessment step 420 has been performed, and the test 415 indicates that no further dipole moments remain to be assessed in the additional material, another test 425 can now be performed. This test again searches local volumes according to the local affinities table, to see whether any hydrogen donor or hydrogen acceptor sites have not yet been tagged as assessed. Whenever any such site is found, a local volume search is performed, to find the nearest sites of hydrogen bonding propensity of the complementary type. (Note that the possible sites for hydrogen bond formation include a donor site and an acceptor site in the peptide backbone, as well as any sites which may be found in the side chain groups.)

In the presently preferred embodiment, the hydrogen bonding propensities are treated as vectors, but alternatively, they can simply be treated as scalars instead. That is, while the vector restriction is more precise, in practice the vectors will usually be oriented away from the backbone of the peptide chain, so that complementary hydrogen bonding propensities which are sufficiently in proximity are likely to be oriented reasonably close together in any case. However, using the dot product of vector moments for hydrogen bonding propensity, as in the presently preferred embodiment, does provide the advantage that the angle distortions which can be produced by hydrogen bonding can be more directly assessed, since the energetic dependence on these angles is seen more accurately. Thus, as shown in FIG. 4, step 430 preferably sums into the cumulative energy estimate $E_{cum}$ a component $$E_{cum}=E_{cum}+(H_1 H_2)K_4 d^{-n},$$

where $H_1$ and $H_2$ are the oriented values of the hydrogen bond components. Preferably the exponent n which gives the distance dependence is 10, but alternatively a larger value for this exponent can be used instead, or a simple polynomial could be used instead.

Again, the hydrogen-bonding potential site thus assessed is tagged; if the complementary bonding site found was also a portion of the candidate structure, and had not yet been assessed, it is tagged as assessed. In assessing contributions from hydrogen bonding, it may be useful to impose a maximum on the energetic contribution estimated from any one hydrogen bond, as well as a threshold level below which estimated contributions will not be counted.

It should be noted that modifications to the hydrogen-bonding propensity magnitudes can optionally be made, to allow for effects due to localization. For example, a "bifurcated" hydrogen bond (where, e.g., two donors are in proximity to one acceptor) is preferably estimated using a slightly different constant. (Alternatively, such bifurcated bonds can be treated as a separate case, and their contributions evaluated using a three-body formula.)

VAN DER WAALS CONTRIBUTIONS

After repetition of step 425 indicates that no hydrogen donors or acceptors have not been assessed, a step 440 is preferably performed to estimate the remaining portion of van der Waals force contribution. An estimate for this contribution commonly used is a so-called 6-12 law, where a 6-th power attractive force is balanced by a 12-th power repulsive force to give an energetic minimum at the van der Waals radius. (Normally this relationship is simply looked up in a precomputed table, to minimize computation.) The favorable contributions from each individual van der Waals interaction will be relatively small although their total contribution will be important. However, unfavorable contributions found by this assessment may have more significant individual magnitudes.

ENTROPIC CONTRIBUTIONS

In an alternative class of embodiments, an optional additional step 450 is used to take account of entropic contribution and steric hindrance. This is of smaller importance than many of the other contributions, and can optionally be omitted.

ANGLE-DEPENDENT STRAIN CONTRIBUTIONS

Next, a step 460 is preferably used to take account of angle strains induced in the added structure or in the original structure. That is, where the dihedral angles of the added structure are locally not equal to those of a stable free space structure, the unfavorable energetic contribution due to bond distortion can be estimated.

HYDRATION CONTRIBUTIONS

Finally, a step 470 is used to assess hydration energies. Assessment of hydration energies, at least at the surfaces of the protein, is typically extremely simple, since these can, to a good approximation, be treated simply as characteristic of the various groups used. Thus, a polar group or a charged group exposed to the solution will in general be favored over an aliphatic group.

A volume exclusion calculation is preferably included as part of this calculation: the exclusion calculation (which can be implemented in a variety of ways, e.g. by applying simple tests to each local neighborhood in the shell map 240) finds which atoms and groups are exposed (by gaps in the atomic packing) to interact with the solution.

INCREMENTAL MACROMOLECULE CONSTRUCTION

Dynamic Programming

Thus, the estimation procedure shown in FIG. 4 provides the detailed steps preferably used in reevaluation step 380, and also preferably in step 160 as will be discussed below.

Figure 5:
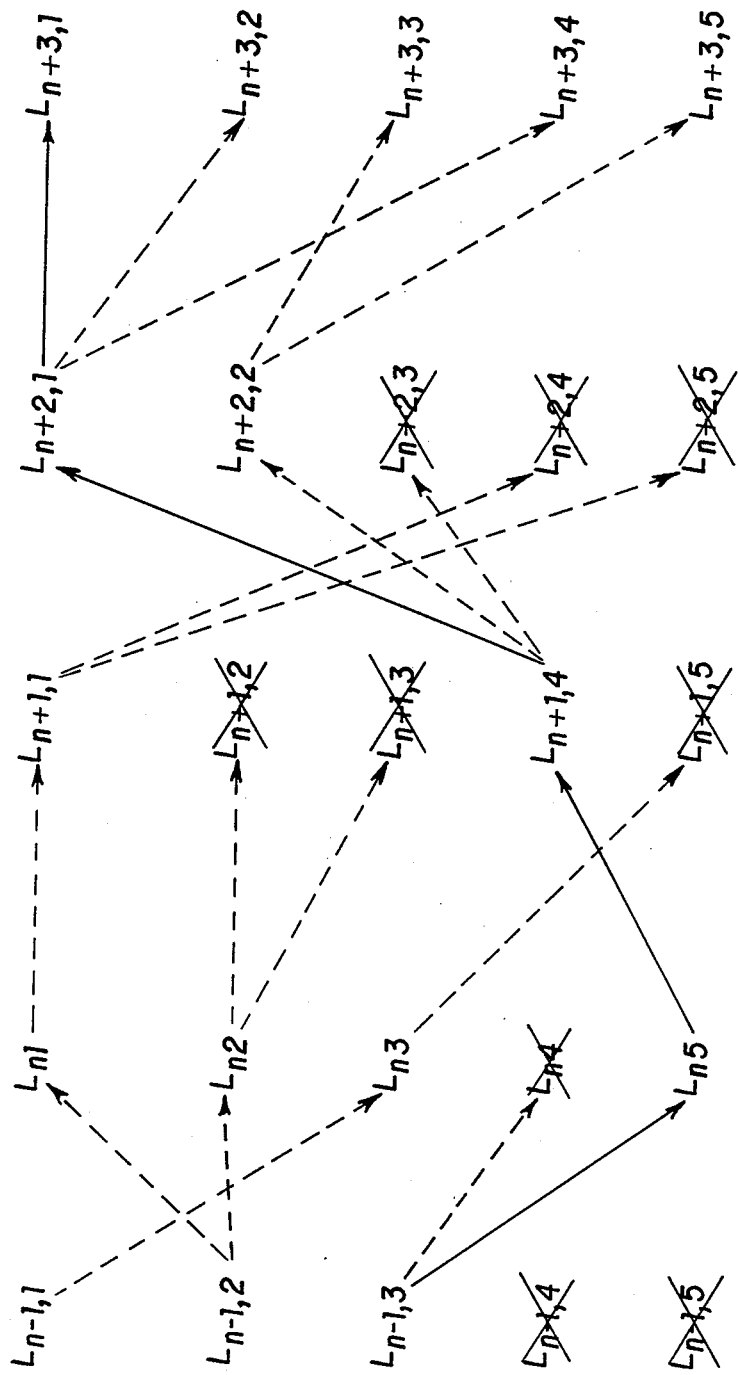
FIG. 5 schematically shows the operation of a dynamic programming method which permits correct "look-ahead" decisions to be made in selecting a candidate for the next portion of a polypeptide structure being incrementally constructed.

In the presently preferred embodiment, a dynamic programming method is used to obtain a "look ahead" optimization. Dynamic programming is a known technique, which is shown schematically in FIG. 5. FIG. 5 shows a sample dynamic programming matrix which is 5 wide and 6 deep. $L_{(N+1,1)}$ represents the cumulative hypothesis which has the highest figure of merit at stage $N+1$. Similarly, $L_{(N+1,2)}$ represents the hypothesis which had the second highest figure of merit at this stage, $L_{(N-1,2)}$ represents the hypothesis which had the second highest figure of merit at stage $N-1$, and so forth. The dotted arrow shown in FIG. 5 indicates the sequencing connections between the different hypotheses. That is, hypothesis $L_{(N+1,1)}$ represents a chain of hypotheses $L_{(N-2,1)}$, $L_{(N-1,2)}$, $L_{(N,1)}$, and $L_{(N+1,1)}$. Similarly, the hypothesis $L_{(N+1,4)}$ represents the chain of hypotheses $L_{(N-1,3)}$, $L_{(N,5)}$, $L_{(N+1,4)}$.

Dynamic programming is a known method for preserving hypotheses which are not locally the best hypothesis, in the expectation that a hypothesis which is locally non-optimal may later turn out to have been the optimal hypothesis. This avoids the problem of getting stuck at a hypothesis which locally is favorable but which turns out to be a dead end.

In dynamic programming methods, multiple hypotheses are retained as candidates at each step of the procedure. In the example shown in FIG. 5, five hypotheses are carried forward as candidates at each step. In the application of dynamic programming to the present invention, the hypotheses would preferably be distinguished on the same basis as library building blocks are distinguished. For example, a glycine residue might be one hypothesis, a proline residue might be another hypothesis, a glycine residue preceded by the less preferred cis configuration of the peptide backbone might be another hypothesis, an alanine side chain might be another hypothesis, and there might be no fifth hypothesis, i.e. no hypothesis which would meet the threshold criteria for not rejecting a hypothesis out of hand.

The sample dynamic programming relation shown in FIG. 5 represents an unusually complex matrix. In fact, complexity of the sort indicated suggests that the dynamic programming operation should be carried more levels "deep". The "depth" of a dynamic programming operation corresponds to the number of decision frames within which a temporarily disfavored hypothesis can be expected to show its merits, if any. In the example shown in FIG. 5, it can be seen that five levels deep is barely enough, since only as of decision frame $N+3$ has it become clear that the preferable hypothesis at frame $N-1$ was hypothesis $L_{(N-1,1)}$.

To more clearly show how hypotheses are chained together, in FIG. 5, the hypothesis chain which results in the preferred hypothesis as of stage $N+3$ has been indicated by solid lines. Thus, it may be seen that this hypothesis $L_{(N+3,1)}$ is descended from hypotheses $L_{(N+2,1)}$, $L_{(N+1,4)}$, $L_{(N,5)}$, and $L_{(N-1,3)}$. That is, the hypothesis which appears clearly most preferable by frame $N+3$ was at one time ranked as low as fifth in the hypothesis set.

Figure 3:
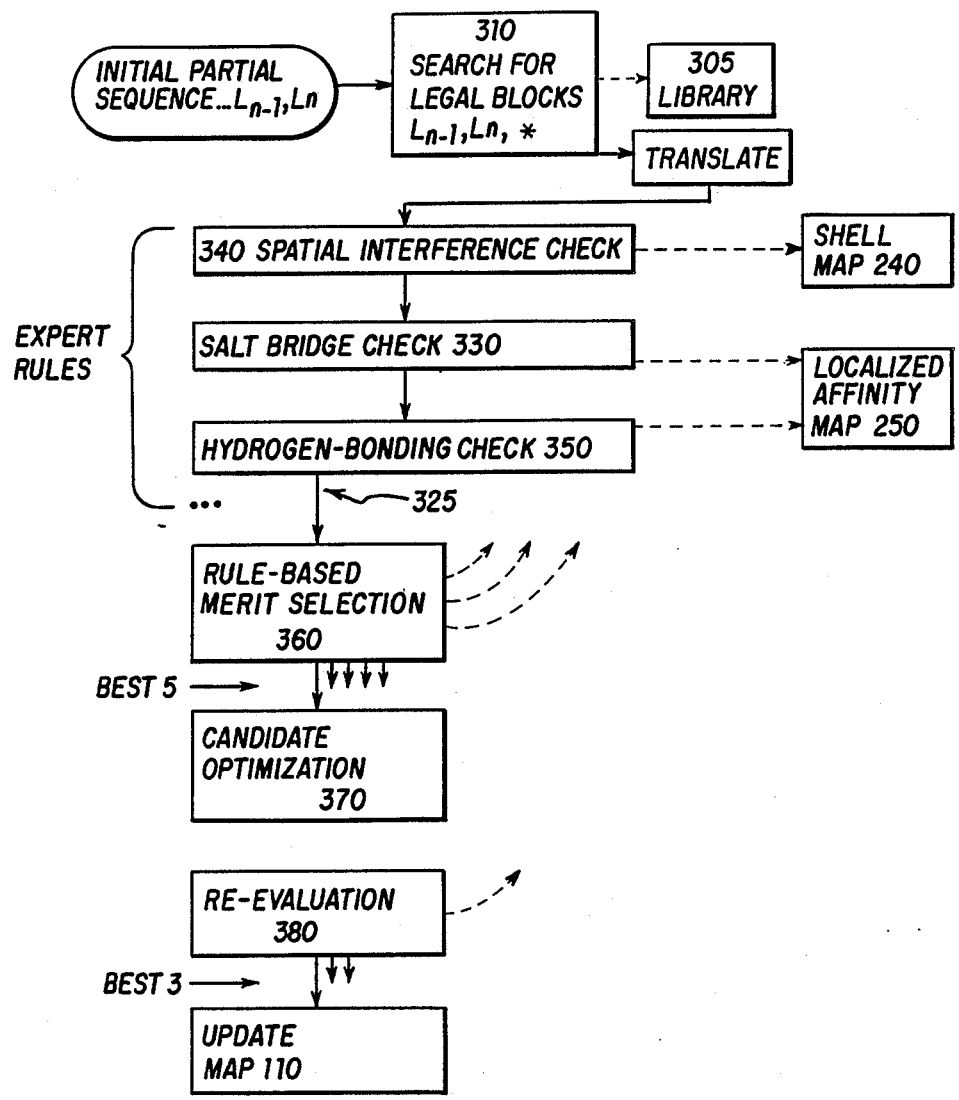
FIG. 3 shows the steps in selection of candidates for the next portion of a polypeptide structure being incrementally constructed.

Thus, the incremental construction step 140 shown in FIG. 3 is preferably further modified by being implemented as part of a dynamic programming process. That is, step 140 in FIG. 1 is preferably performed in parallel. Each of the five hypotheses carried forward is used as input to the incremental construction block 140 shown in FIG. 3, and the reevaluation step 380 of each iteration of the incremental construction block 140 will produce three candidates. An additional reevaluation step 145 is preferably used to call the 15 candidates thus produced down to a maximum of 5 candidates which form the next generation of hypothesis.

BACKTRACKING

Backtracking, with a "good enough" acceptance threshold figure, can (less preferably) be used instead of dynamic programming to implement a "look-ahead" decision-making capability. However, backtracking has some inherent difficulty with computational scaling. Optionally, this can be accommodated by requiring backtracking of more than one residue at a time. However, the dynamic programming methods discussed above are more preferable.

In particular, the combination of dynamic programming with limited backtracking is particularly advantageous. That is, when the dynamic programming method hits an impasse, the dynamic programming matrix may be temporarily widened (and/or deepened), so that new hypotheses can be introduced at earlier steps and propagated forward.

Of course, in backtracking procedures generally it is useful to exclude the hypotheses which led to the impasse, to make sure that the backtracking procedure does find additional candidates. However, the exclusion of the dead-end hypotheses cannot be done too broadly, since of course it will typically not be known where the dead-end hypothesis diverges from the (hoped for) more viable chain of candidate hypotheses. This can be done by backtracking one step at a time; but such a procedure scales very unfavorably, which is why the computational demands of backtracking procedures must be carefully delimited.

Similarly, the possibility of operator intervention (in an "expert-assistant" embodiment) permits the operator to rescue the dynamic programming process from any impasses which it might encounter.

INITIALIZATION AND CLOSURE

To begin the incremental construction process, the most preferable way is to backtrack into the existing structure for the full depth of the dynamic programming algorithm, and carry the existing end sequence (i.e. the sequence of the existing structure leading to the terminal group) as one of the hypotheses in the dynamic programming algorithm. This means that adaptation of the incremental construction process to accommodate the structural constraints on the existing sequence (without being too tightly bound by those constraints) is straightforward).

When the construction process is found to be close to its end (which is detected by monitoring progress along the overall path determined by step 120), a modification to the algorithmic methods otherwise used is preferably used to assure a smooth transition. This modification, and that necessary to do the initialization 130 to start up the incremental construction method, will not be discussed.

POST-CONSTRUCTION OPTIMIZATION

Preferably a final optimization step is applied, after the chain of amino acid residues has been specified. This additional optimization helps to ensure that the best solution which has been found is acceptable. Thus, a variety of energetic optimization techniques may be applied at this stage, including procedures such as those detailed above or procedures according to any of the known techniques for energetic optimization.

This final optimization step can also be used to make a final decision between candidates. For example, the chain-closing step may be allowed to provide the best 3 candidates (from the dynamic programming algorithm), and selection made from among those three candidates on the basis of figures of merit estimated after the final energetic optimization.

PRODUCT MANUFACTURE

Polypeptide sequences, generated by the methods described above, are manufactured by translating them into genetic sequences, as will now be discussed.

The genetic code is sufficiently redundant that there are in many instances multiple possible codons for any one amino acid. Therefore, codon usage rules, which are also well understood by those of skill in the art, can be utilized for the preparation of optimized genetic sequences for coding in any desired organism. (See, for example, Ikemura, *J. Mol. Biol.* 151:389-409 (1981) (which is hereby incorporated by reference)).

Generally, it is possible to utilize the cDNA sequences obtained from the light and heavy chains of the variable region of the original antibody as a starting point. These sequences can then be joined by means of genetic linkers coding for the peptide linker candidates elucidated by the methods of the invention. The genetic sequence can be entirely synthesized de novo or fragments of cDNA can be linked together with the synthetic linkers, as described.

A large source of hybridomas and their corresponding monoclonal antibodies are available for the preparation of sequence coding for the H and L chains of the variable region. As indicated previously, it is well known that most "variable" regions of antibodies of a given class are in fact quite constant in their three dimensional folding pattern, except for certain specific hypervariable loops. Thus, in order to choose and determine the specific binding specificity of the single chain binding protein of the invention it becomes necessary only to define the protein sequence (and thus the underlying genetic sequence) of the hypervariable region. The hypervariable region will vary from binding molecule to molecule, but the remaining domains of the variable region will remain constant for a given class of antibody.

Source mRNA can be obtained from a wide range of hybridomas. See for example the catalogue *ATCC Cell Lines and Hybridomas,* December 1984, American Type Culture Collection, 20309 Parklawn Drive, Rockville, Md. 20852, U.S.A., at pages 5-9. Hybridomas secreting monoclonal antibodies reactive with a wide variety of antigens are listed therein, are available from the collection, and usable in the invention. Of particular interest are hybridomas secreting antibodies which are reactive with viral antigens, tumor associated antigens, lymphocyte antigens, and the like. These cell lines and others of similar nature can be utilized to copy mRNA coding for the variable region or determine amino acid sequence from the monoclonal antibody itself. The specificity of the antibody to be engineered will be determined by the original selection process. The class of antibody can be determined by criteria known to those skilled in the art. If the class is one for which there is a three-dimensional structure, one needs only to replace the sequences of the hyper-variable regions (or complementary determining regions). The replacement sequences will be derived from either the amino acid sequence or the nucleotide sequence of DNA copies of the mRNA.

It is to be specifically noted that it is not necessary to crystallize and determine the 3-D structure of each variable region prior to applying the method of the inventions. As only the hypervariable loops change drastically from variable region to variable region (the remainder being constant in the 3-D structure of the variable region of antibodies of a given class), it is possible to generate many single chain 3-D structures from structures already known or to be determined for each class of antibody.

Expression vehicles for production of the molecules of the invention include plasmid or other vectors. In general, such vectors containing replicon and control sequences which are derived from species compatible with a host cell are used in connection with the host. The vector ordinarily carries a replicon site, as well as specific genes which are capable of providing phenotypic selection in transformed cells. For example, E. coli is readily transformed using pBR322, a plasmid derived from an E. coli species. pBR322 contains genes for ampicillin and tetracycline resistance, and thus provides easy means for identifying transformed cells. The pBR322 plasmid or other microbial plasmid must also contain, or be modified to contain, promoters which can be used by the microbial organism for expression of its own proteins. Those promoters most commonly used in recombinant DNA construction include the beta lactamase, lactose promoter systems, lambda phage promoters, and the tryptophan promoter systems. While these are the most commonly used, other microbial promoters have been discovered and can be utilized.

For example, a genetic construct for a single chain binding protein can be placed under the control of the leftward promoter of bacteriophage lambda. This promoter is one of the strongest known promoters which can be controlled. Control is exerted by the lambda repressor, and adjacent restriction sites are known.

The expression of the single chain antibody can also be placed under control of other regulatory sequences which may be homologous to the organism in its untransformed state. For example, lactose dependent E. coli chromosomal DNA comprises a lactose or lac operon which mediates lactose utilizing by elaborating the enzyme beta-galactosidase. The lac control elements may be obtained from bacteriophage lambda plac5, which is infective for E. coli. The lac promoter-operator system can be induced by IPTG.

Other promoter/operator systems or portions thereof can be employed as well. For example, colicin El, galactose, alkaline phosphatase, tryptophan, xylose, tac, and the like can be used.

Of particular interest is the use of the $O^L/P^R$ hybrid lambda promoter (see for example U.S. patent application Ser. No. 534,982 filed Sept. 3, 1983, now abandoned and herein incorporated by reference).

Other preferred hosts are mammalian cells, grown in vitro in tissue culture, or in vivo in animals. Mammalian cells provide post translational modifications to immunoglobulin protein molecules including correct folding or glycosylation at correct sites.

Mammalian cells which may be useful as hosts include cells of fibroblast origin such as VERO or CHO-K1, or cells of lymphoid origin, such as the hybridoma SP2/0-AG14 or the myeloma P3x63Sg8, and their derivatives.

Several possible vector systems are available for the expression of cloned single chain binding proteins in mammalian cells. One class of vectors utilizes DNA elements which provide autonomously replicating extra-chromosomal plasmid, derived from animal viruses such as bovine papilloma virus, polyoma virus, or SV40 virus. A second class of vectors relies upon the integration of the desired gene sequences into the host cell chromosome. Cells which have stably integrated the introduced DNA into their chromosomes can be selected from also introducing drug resistance genes such as E. coli GPT or Tn5neo. The selectable marker gene can either be directly linked to the DNA gene sequences to be expressed, or introduced into the same cell by cotransfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., Mol. Cel. Biol., 3:280 (1983) (which is hereby incorporated by reference), and others.

Another preferred host is yeast. Yeast provides substantial advantages in that it can also carry out post translational peptide modifications including glycosylation. A number of recombinant DNA strategies exist which utilize strong promoter sequences and high copy number of plasmid which can be utilized for production of the desired proteins in yeast. Yeast recognizes leader sequences on cloned mammalian gene products, and secretes peptides bearing leader sequences (i.e., pre-peptides).

Any of a series of yeast gene expression systems incorporating promoter and termination elements from the actively expressed genes coding for glycolytic enzymes produced in large quantities when yeast are grown in mediums rich in glucose can be utilized. Known glycolytic genes can also provide very efficient transcription control signals. For example, the promoter and terminator signals of the phosphoglycerate kinase gene can be utilized.

Once the strain carrying the single chain building molecule gene has been constructed, the same can also be subjected to mutagenesis techniques using, chemical agents or radiation, as is well known in the art. From the colonies thus obtained, it is possible to search for those producing binding molecules with increased binding affinity. In fact, if the first linker designed with the aid of the computer fails to produce an active molecule, the host strain containing the same can be mutagenized. Mutant molecules capable of binding antigen can then be screened by means of a routine assay.

SOME ALTERNATIVE EMBODIMENTS

As discussed above, the innovative techniques disclosed herein can be used to construct a tremendous variety of macromolecular structures. These include not only single-chain antibodies, but also other binding proteins, enzymes, enzyme cofactors and inhibitors, nucleic acid complexes, hormones, vaccines, toxins, and many others.

The innovative methods disclosed could also be applied to situations where it was desired to add nonpeptide structure. The key to such applications generally is the ability to define a set of "building blocks" which is large enough to be useful (in the context of whatever problem is being solved), but which is small enough to be not overwhelming in storage and computational demands. For example, one optional application would be to customize the lipid portion of lipoproteins or the carbohydrate portions of glycoproteins.

Other embodiments of the present invention not only permit modification of a wider range of chemical structures, but also permit a wider range of modifications.

For example, where a structure is initially specified which has multiple free ends, completion of the structure can be performed by adding units incrementally onto all of the free ends in parallel. This permits the joint interaction of the units being constructed to be taken into account without presenting an impossible computational burden. In embodiments of this type, a library which includes the standard varieties of reverse turn is preferably used, so that each of the possible closures can be examined as a hypothesis at each step, so that the structure can be rapidly completed. Again, this may be advantageous when it is desired to simulate a complex natural structure by taking only a portion of that natural structure as the starting point and building outwardly therefrom.

Once a new structure has been designed, built, and demonstrated to have at least partial functionality, mutagenic methods can be used to induce random variations in the protein product being expressed. For example, site-specific mutagenesis can be used to specifically mutate the genetic material which codes for the customized protein. While it may seem odd to immediately induce mutations on the recombinant-DNA structure so newly developed, this can provide a useful way to do a final empirical optimization of the design developed using the methods set forth above.

As will be recognized by those skilled in the art, the present application sets forth an extremely broad range of novel concepts, which can be modified and varied in a large variety of ways. Accordingly, the scope of the present invention is defined only by the claims.

What is claimed is:

1. A computer-assisted method for modifying a structure using at least two blocks disposed between a starting point and an end point, comprising the steps of:
   (a) mapping onto said starting point a first one of said blocks to produce information including XYZ coordinates and at least one non-spatial parameter of said first one of said blocks;
   (b) incrementally adding a second one of said blocks to said first one of said blocks or to said end point by mapping to produce information including XYZ coordinates and at least one non-spatial parameter of said second one of said blocks; and
   (c) synthesizing the structure with the first one and second one of said blocks as specified by steps (a) and (b), respectively.

2. The method of claim 1, wherein said non-spatial parameter of step (a) or of said (b) is a local dielectric constant.

3. The method of claim 1, wherein said non-spatial parameter of step (a) or of said (b) is a hydrogen-bonding propensity.

4. The method of claim 1, wherein said non-spatial parameter of step (a) or of said (b) is a localized electrostatic charge.

5. The method of claim 1, further comprising a step (d) between steps (b) and (c) of incrementally adding a third one of said blocks to said first one of said blocks or to said second one of said blocks or to said end point by mapping to produce information including XYZ coordinates and at least one non-spatial parameter of said second one of said blocks, and
   wherein step (c) synthesizes the structure with the first one, the second one, and the third one of said blocks as specified by steps (a), (b) and (d).

6. The method of claim 1, wherein said blocks are selected from a library, wherein some of said blocks within said library contain peptide sequences.

7. The method of claim 1, wherein said blocks are selected from a library which provides, for each block therein, multiple precomputed parameters, including a first parameter for estimating dependence of energy on a second parameter (including conformational parameters) of said block.

8. A computer-assisted method for modifying a structure using at least two blocks to bridge the structure between a starting point and an end point, comprising the steps of:
   (a) mapping onto said starting point a first one of said blocks to produce information including XYZ coordinates and at least one non-spatial parameter of said first one of said blocks;
   (b) incrementally adding a second one of said blocks to said first one of said blocks or to said end point by mapping to produce information including XYZ coordinates and at least one non-spatial parameter of said second one of said blocks, said second one of said blocks ending at said end point;
   (c) synthesizing the structure with the first one and second one of said blocks as specified by steps (a) and (b), respectively, so that the first one and second one of said blocks bridge the structure between said starting point and said end point.

9. A computer-assisted method for modifying a structure using n blocks to bridge the structure between a starting point and an end point, where n is a positive integer equal to or greater than 8, comprising the steps of:
   (a) mapping onto said starting point a first one of said blocks to produce information including XYZ coordinates and at least one non-spatial parameter of said first one of said blocks;
   (b) incrementally adding a second one of said blocks to said first one of said blocks or to said endpoint by mapping to produce information including XYZ coordinates and at least one non-spatial parameter of said second one of said blocks; and
   (c) incrementally adding x one of said blocks, where x is a positive integer and is greater than 2, to said x−1 one of said blocks or to said x−2 one of said blocks by mapping to produce information including XYZ coordinates and at least one non-spatial parameter of said x one of said blocks;
   (d) repeating step (c) for incrementally adding x one of said blocks until x=n, so that n blocks bridge the structure between the starting point and the end point;
   (e) synthesizing the structure with the n blocks as specified by steps (a), (b), (c), and (d) so that the n blocks bridge the structure between said starting point and said end point.

10. The method of claim 9, wherein one or more of said n blocks is optimized using a local dielectric constant.

11. The method of claim 9, wherein one or more of said n blocks is optimized using hydrophobicity.

12. The method of claim 9, wherein one or more of said blocks is optimized using hydrogen bonding propensity.

13. The method of claim 9, wherein one or more of said n blocks is optimized using a dipole moment.

14. The method of claim 9, wherein one or more of said n blocks is optimized using a localized electrostatic charge.

15. The method of claim 9, further comprising a step (f) between step (d) and step (e) of performing steps (a), (b) and (c) using expert rules and/or rule-based merit selection.

16. The method of claim 9, wherein steps (a), (b), and (c) use an interactive computer process which,
    makes available to a user a graphics representation of said XYZ coordinates and said at least one non-spatial parameter, and
    performs ranking of blocks for steps (a), (b) and (c).

17. The method of claim 16,
    wherein said interactive computer process further comprises, permitting the user to exclude some of the blocks from consideration.

18. The method of claim 16, wherein said interactive computer process
    allows for the user to engage in backtracking in performing steps (a), (b) and/or (c).

19. The method of claim 9, wherein steps (a), (b) and/or (c) include the step of allowing the user to utilize look ahead optimization.

20. A computer-assisted method for modifying a structure using at least two blocks disposed between a starting point and an end point, comprising the steps of:
    (a) mapping onto said starting point a first one of said blocks to produce information including XYZ coordinates and at least one non-spatial parameter of said first one of said blocks;
    (b) incrementally adding a second one of said blocks to said first one of said blocks or to said end point by mapping to produce information including XYZ coordinates and at least one non-spatial parameter of said second one of said blocks peptide sequences of length n (wherein n is between 2 and 4 inclusive),
    said blocks being selected (at least in part) for fit with respect to said localized additional characteristics;
    (c) obtaining the information used in steps (a) and (b) from a library having peptide sequence information; and
    (d) synthesizing the structure with the first one and second one of said blocks as specified by steps (a) and (b), respectively.

21. The method of claim 20, wherein said library of step (c) includes automatic mechanisms for updating said library with parameters for additional blocks as those parameters become available.

22. A computer-assisted method for modifying a structure using at least two blocks disposed between a starting point and an end point, comprising the steps of:
    (a) mapping onto said starting point a first one of said blocks to produce information including XYZ coordinates and at least one non-spatial parameter of said first one of said blocks;
    (b) incrementally adding a second one of said blocks to said first one of said blocks or to said endpoint by mapping to produce information including XYZ coordinates and at least one non-spatial parameter of said second one of said blocks; and
    (c) performing (a) and (b) using expert rules and/or rule-based merit selection; and
    (d) synthesizing the structure with the first one and second one of said blocks as specified by steps (a) and (b), respectively.

23. A computer-assisted method for modifying a structure using at least two blocks disposed between a starting point and an end point, comprising the steps of:
    (a) mapping onto said starting point a first one of said blocks to produce information including XYZ coordinates and at least one non-spatial parameter of said first one of said blocks;
    (b) incrementally adding a second one of said blocks to said first one of said blocks or to said endpoint by mapping to produce information including XYZ coordinates and at least one non-spatial parameter of said second one of said blocks;
    (c) said first one and/or said second one of said blocks being selected by a method which includes the substeps of:
        (1) retrieving data from a library to define at least one candidate set for said first one and/or said second one of said blocks,
        (2) culling said candidate set of substep (1), using one or more non-spatial parameter(s), to remove unacceptable blocks from said candidate set to produce a reduced candidate set of blocks, and
        (3) optimizing adjustable parameters of blocks of said reduced candidate set of blocks disposed between said starting point and said end point; and
    (d) synthesizing the structure with the first one and second one of said blocks as specified by steps (a) and (b), respectively, so that the first one and second one of said blocks are disposed between said starting point and said end point.

24. A computer-assisted method for modifying a structure using at least two blocks disposed between a starting point and an end point, comprising the steps of:
    (a) mapping onto said starting point a first one of said blocks to produce information including XYZ coordinates and at least one non-spatial parameter of said first one of said blocks;
    (b) incrementally adding a second one of said blocks to said first one of said blocks or to said end point by mapping to produce information including XYZ coordinates and at least one non-spatial parameter of said second one of said blocks;
    (c) said first one and/or said second one of said blocks being selected by a method which includes the substeps of;
        (1) retrieving data from a library to define a coordinate set of blocks, and
        (2) ranking said candidate set, and accordingly removing low-ranked blocks to provide a reduced candidate set of blocks disposed between said starting point and said end point; and
    (d) synthesizing the structure with the first one and second one of said blocks as specified by steps (a) and (b), respectively, so that the first one and second one of said blocks are disposed between said starting point and said end point.

25. A computer-assisted method for modifying a structure using at least two blocks disposed between a starting point and an end point, comprising the steps of:
    (a) mapping onto said starting point a first one of said blocks to produce information including XYZ coordinates and at least one non-spatial parameter of said first one of said blocks;
    (b) incrementally adding a second one of said blocks to said first one of said blocks or to said endpoint by mapping to produce information including XYZ coordinates and at least one non-spatial parameter of said second one of said blocks;
(c) said first one and/or said second one of said blocks being selected by a method which includes the substeps of:
  (1) retrieving data from a library to define at least one candidate set for said first one and/or said second one of said blocks,
  (2) ranking said candidate set of blocks, and accordingly removing low-ranked blocks in said candidate set to provide a reduced candidate set of blocks,
  (3) optimizing adjustable parameters of blocks of said reduced candidate set of blocks, and
  (4) re-ranking said reduced candidate set of blocks, and accordingly removing low-ranked blocks from said reduced candidate set to provide a further-reduced candidate set of blocks disposed between said starting point and said end point; and
(d) synthesizing the structure with the first one and second one of said blocks as specified by steps (a) and (b), respectively, so that the first one and second one of said blocks are disposed between said starting point and said end point.

26. An interactive computer-assisted method for modifying a structure using at least two blocks disposed between a starting point and an end point, comprising the steps of:
(a) mapping onto said starting point a first one of said blocks to produce information including XYZ coordinates and at least one non-spatial parameter of said first one of said blocks;
(b) incrementally adding a second one of said blocks to said first one of said blocks or to said end point by mapping to produce information including XYZ coordinates and at least one non-spatial parameter of said second one of said blocks, using an interactive computer which,
  makes available to a user a graphics representation of information including XYZ coordinates and/or at least one non-spatial parameter of possible blocks for step (b) and the structure, and
  performs ranking of said possible blocks for step (b); and
(c) synthesizing the structure with the first one and second one of said blocks as specified by steps (a) and (b), respectively, so that the first one and second one of said blocks are disposed between said starting point and said end point.

27. A computer-assisted process outputting at least two blocks to be disposed between a starting point and an end point of a structure, comprising the steps of:
(a) mapping onto said starting point of said structure a first one of said blocks to produce information including XYZ coordinates and at least one non-spatial parameter of said first one of said blocks;
(b) incrementally adding a second one of said blocks to said first one of said blocks by mapping to produce parameter of said second one of said blocks; and
(c) outputting said first one and said second one of said blocks to be disposed between said starting point and said end point of said structure.

28. A product produced by a computer-assisted process, said product comprising a structure with a first block and a second block, said first and second blocks disposed between a starting point and an end point of said structure, said computer assisted process comprising the steps of:
(a) mapping a structure having a starting point and an end point;
(b) mapping onto said starting point the first block to produce information including XYZ coordinates and at least one non-spatial parameter of said first block;
(c) incrementally adding the second block to said first block or to said end point by mapping to produce information including XYZ coordinates and at least one non-spatial parameter of said second block.

29. A product produced by a computer-assisted process, said product comprising a structure with a first block and a second block, said first and second blocks bridging the structure between a starting point and an end point of said structure, said computer assisted process comprising the steps of:
(a) mapping the structure having a starting point and an end point;
(b) mapping onto said starting point a first one of said blocks to produce information including XYZ coordinates and at least one non-spatial parameter of the first block;
(c) incrementally adding the second block to the first block or to said end point by mapping to produce information including XYZ coordinates and at least one non-spatial parameter of the second block, the second block ending at the end point.

30. A product produced by a computer-assisted process, said product comprising a structure with n blocks, said n blocks bridging the structure between a starting point and an end point of said structure, where n is a positive integer equal to or greater than 2, said computer assisted process comprising the steps of:
(a) mapping the structure having a starting point and an end point;
(b) mapping onto said starting point a first one of said n blocks to produce information including XYZ coordinates and at least one non-spatial parameter of said one of said blocks;
(c) incrementally adding a second one of said n blocks to said first one of said n blocks or to said end point by mapping to produce information including XYZ coordinates and at least one non-spatial parameter of said second one of said n blocks;
(d) incrementally adding x one of said n blocks, where x is a positive integer and is greater than 2, to said x−1 one of said n blocks or to said x−2 one of said n blocks by mapping to produce information including XYZ coordinates and at least one non-spatial parameter of said x one of said n blocks;
(e) repeating step (d) for incrementally adding x one of said n blocks until x=n, so that n blocks bridge the structure between the starting point and the end point.

31. A computer-assisted process outputting n blocks for modifying a structure, where the n blocks bridge the structure between a starting point and an end point, where n is a positive integer equal to or greater than 2, comprising the steps of:
(a) mapping onto said starting point a first one of said blocks to produce information including XYZ coordinates and at least one non-spatial parameter of said first one of said blocks;
(b) incrementally adding a second one of said blocks to said first one of said blocks or to said endpoint by mapping to produce information including XYZ coordinates and at least one non-spatial parameter of said second one of said blocks;

(c) incrementally adding x one of said blocks, where x is a positive integer and is greater than 2, to said x−1 one of said blocks or to said x−2 one of said blocks by mapping to produce information including XYZ coordinates and at least one non-spatial parameter of said x one of said blocks;

(d) repeating step (c) for incrementally adding x one of said blocks until x=n, so that n blocks bridge the structure between the starting point and the end point;

(e) outputting the structure with the n blocks as specified by steps (a), (b), (c), and (d) so that the n blocks bridge the structure between said starting point and said end point.

* * * * *

UNITED STATES PATENT AND TRADEMARK OFFICE
CERTIFICATE OF CORRECTION

PATENT NO. : 4,939,666
DATED : July 3, 1990
INVENTOR(S) : HARDMAN

It is certified that error appears in the above-identified patent and that said Letters Patent is hereby corrected as shown below:

In Claim 2, line 2, delete "said" and substitute therefor --step--.

In Claim 3, line 2, delete "said" and substitute therefor --step--.

In Claim 4, line 2, delete "said" and substitute therefor --step--.

In Claim 9, line 4, delete "8" and substitute therefor --2--.

In Claim 12, line 2, delete "blocks" and substitute therefor --n blocks--.

In Claim 20, line 12, delete "peptide sequences" and substitute therefor --;--; and lines 13-16, delete "of length n (wherein n is between 2 and 4 inclusive), said blocks being selected (at least in part) for fit with respect to said localized additional characteristics;".

UNITED STATES PATENT AND TRADEMARK OFFICE
CERTIFICATE OF CORRECTION

PATENT NO. : 4,939,666
DATED : July 3, 1990
INVENTOR(S) : HARDMAN

It is certified that error appears in the above-identified patent and that said Letters Patent is hereby corrected as shown below:

In Claim 22, line 12, delete "and"; and line 13, after "performing" insert "steps".

In Claim 26, line 14, after "computer" insert --process--.

In Claim 27, line 10, before "parameter" insert --information including XYZ ordinates and at least one non-spatial--.

Signed and Sealed this

Twenty-seventh Day of May, 1997

Attest:

BRUCE LEHMAN

Attesting Officer     Commissioner of Patents and Trademarks